United States Patent
Beemer et al.

(10) Patent No.: US 9,310,008 B2
(45) Date of Patent: Apr. 12, 2016

(54) TORQUE LIMITED FITTING

(71) Applicant: IDEX Health & Science LLC, Oak Harbor, WA (US)

(72) Inventors: Eric Beemer, Anacortes, WA (US); Craig Graham, Anacortes, WA (US); Mark Hahn, Oak Harbor, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 481 days.

(21) Appl. No.: 13/668,011

(22) Filed: Nov. 2, 2012

(65) Prior Publication Data

US 2013/0233053 A1 Sep. 12, 2013

Related U.S. Application Data

(60) Provisional application No. 61/609,795, filed on Mar. 12, 2012.

(51) Int. Cl.

| | |
|---|---|
| *F16L 37/24* | (2006.01) |
| *F16L 37/244* | (2006.01) |
| *G01N 30/88* | (2006.01) |
| *F16L 21/00* | (2006.01) |
| *B01L 3/00* | (2006.01) |
| *F16L 19/065* | (2006.01) |
| *F16L 15/08* | (2006.01) |

(Continued)

(52) U.S. Cl.
CPC .............. *F16L 37/244* (2013.01); *B01L 3/563* (2013.01); *F16L 15/08* (2013.01); *F16L 19/0237* (2013.01); *F16L 19/065* (2013.01); *F16L 21/00* (2013.01); *G01N 30/88* (2013.01); *B01L 2200/025* (2013.01); *B01L 2200/0631* (2013.01); *B01L 2200/0689* (2013.01); *B01L 2300/0832* (2013.01); *B01L 2300/0851* (2013.01); *G01N 30/6026* (2013.01); *Y10T 137/0447* (2015.04)

(58) Field of Classification Search
CPC ....... F16L 37/24; F16L 37/242; F16L 37/244; F16L 37/2445; F16L 37/248; F16L 37/252; G01N 30/88; B01L 3/563
See application file for complete search history.

(56) References Cited

U.S. PATENT DOCUMENTS

| | | | |
|---|---|---|---|
| 5,183,140 A | 2/1993 | Nicoll | |
| 5,472,598 A | 12/1995 | Schick | |

(Continued)

FOREIGN PATENT DOCUMENTS

| | | | |
|---|---|---|---|
| DE | 4442075 | † | 6/1996 |
| EP | 0450182 A2 | | 10/1991 |
| WO | WO 2006/031386 A2 | | 3/2006 |

OTHER PUBLICATIONS

International Search Report and Written Opinion of the International Searching Authority, International Patent Application No. PCT/US2013/030421, Jul. 4, 2013.

*Primary Examiner* — Laura Martin
*Assistant Examiner* — Alex Devito
(74) *Attorney, Agent, or Firm* — Vinson & Elkins LLP

(57) ABSTRACT

A torque limited fitting is provided having a head and a body, which in certain embodiments may be assembled by an operator. The body of the torque limited fitting has a passageway therethrough for receiving and removably holding tubing. The torque limited fitting may be adapted for use with a flat bottom port, such as in an analytical instrument, like liquid chromatography, gas chromatography, ion chromatography, or in in vitro diagnostic systems.

46 Claims, 21 Drawing Sheets

(51) Int. Cl.
*F16L 19/02* (2006.01)
*G01N 30/60* (2006.01)

(56) References Cited

U.S. PATENT DOCUMENTS

| | | |
|---|---|---|
| 5,525,303 A | 6/1996 | Ford et al. |
| 5,730,943 A | 3/1998 | Ford et al. |
| 6,095,572 A | 8/2000 | Ford et al. |
| 7,954,857 B2 | 6/2011 | Helstern |
| 7,984,933 B2 | 7/2011 | Helstern |
| 2009/0218813 A1 | 9/2009 | Helstern |
| 2010/0224546 A1* | 9/2010 | Ellis et al. ............ 210/232 |
| 2010/0275746 A1* | 11/2010 | Wengreen ............ 81/477 |

\* cited by examiner
† cited by third party

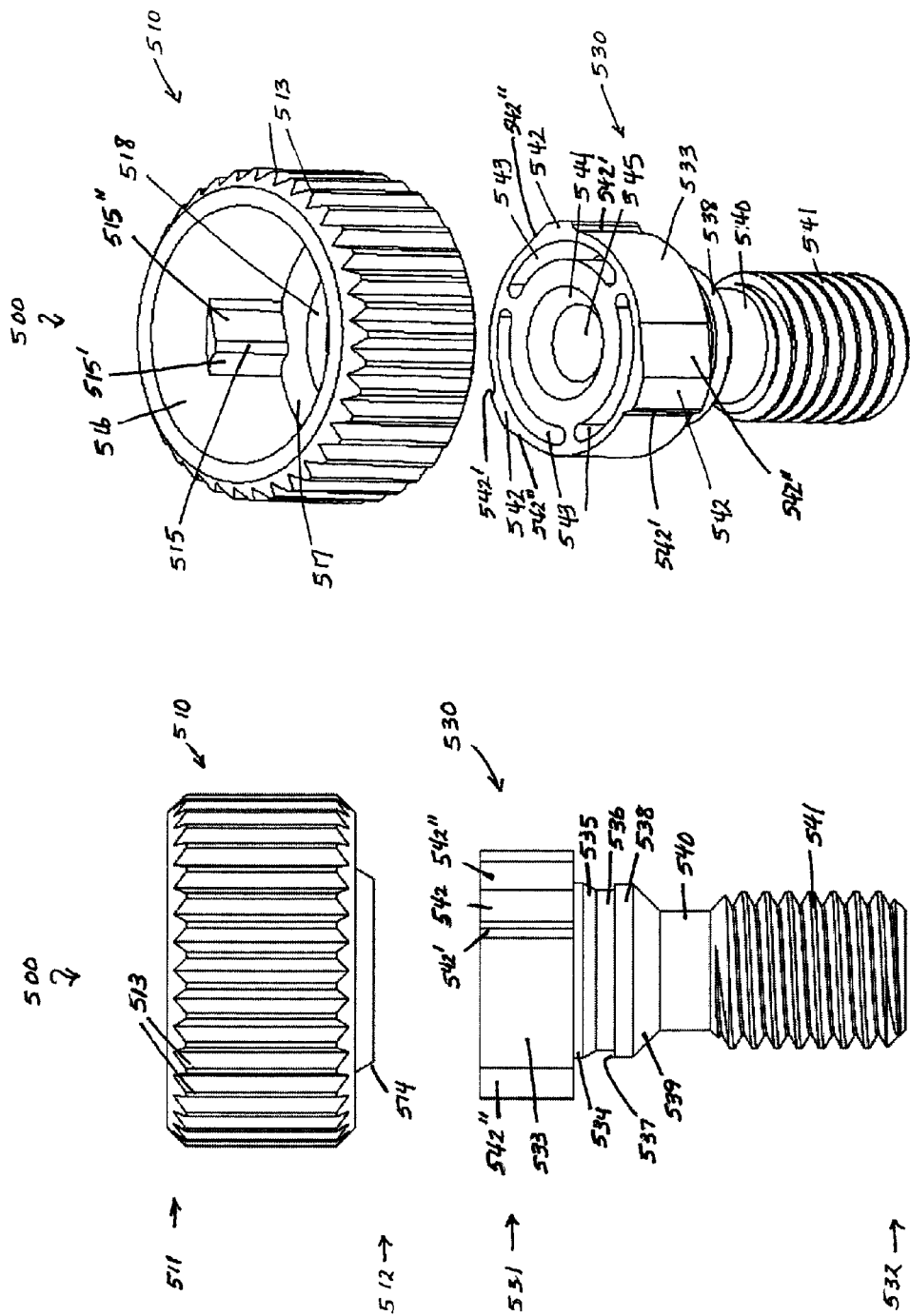

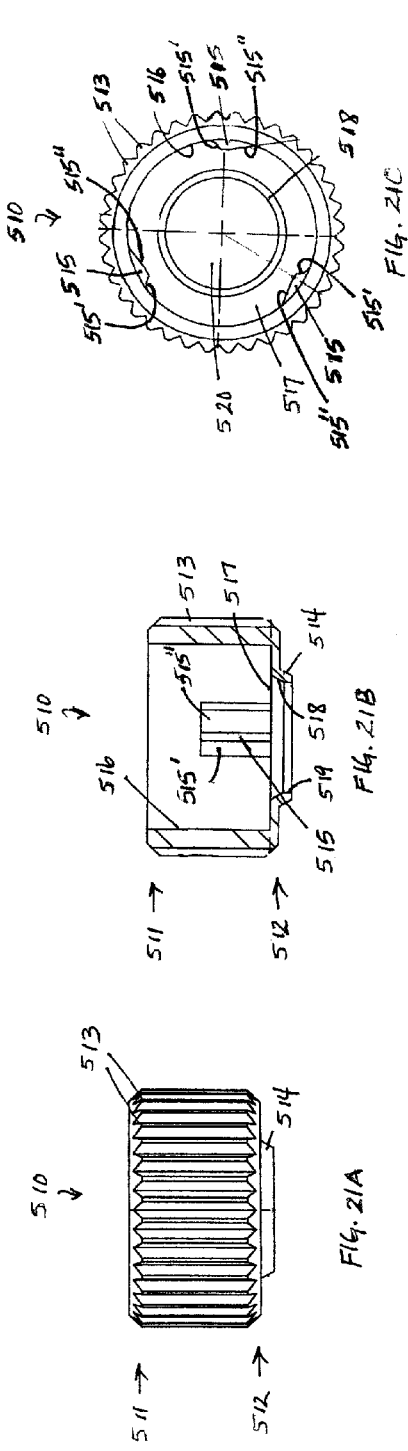
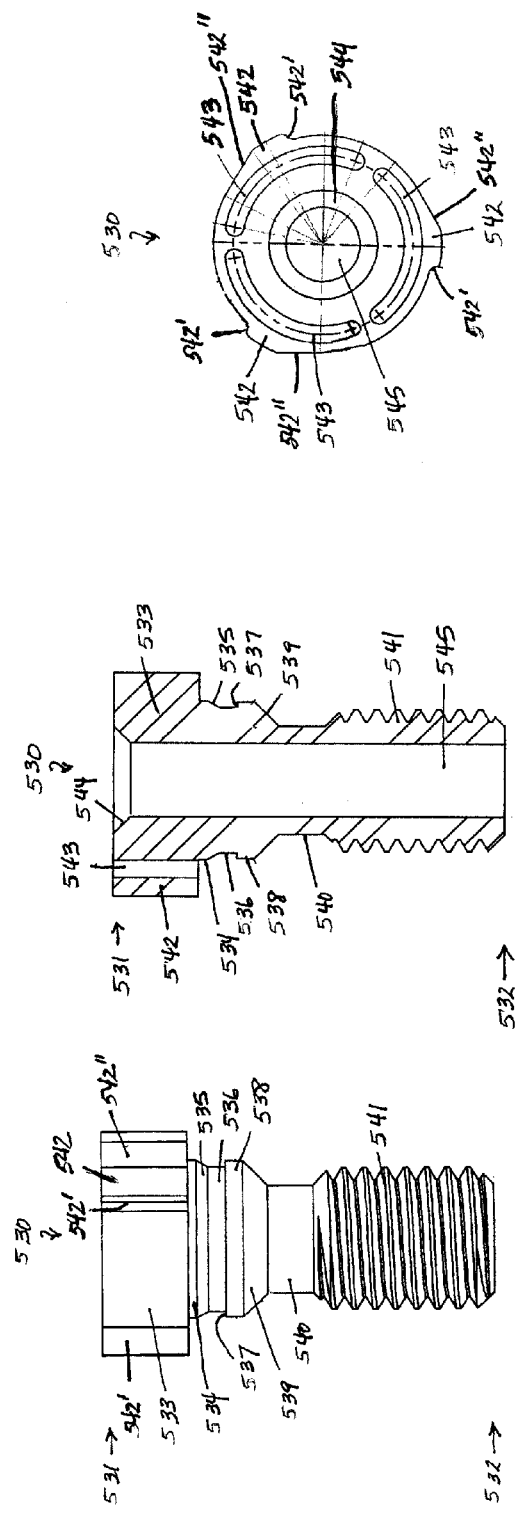
FIG. 21A
FIG. 21B
FIG. 21C
FIG. 22A
FIG. 22B
FIG. 22C

TORQUE LIMITED FITTING

CROSS-REFERENCE TO RELATED APPLICATION

This application claims the benefit of U.S. Provisional Patent Application No. 61/609,795, filed Mar. 12, 2012, which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to fittings for use in connecting tubing and other components of gas chromatography, liquid chromatography, in vitro diagnostic analysis systems, environmental (water) analysis systems, and other analytical systems, and relates more particularly to torque limited fittings.

2. Description of the Related Art

Liquid chromatography (LC), ion chromatography (IC) and gas chromatography (GC) are well-known techniques for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample. Additionally, LC systems may utilize mass spectrometric detection for identification and quantification of the sample, either in addition to, or as an alternative to, the conventional detectors described previously. Ion chromatography relies on the detection of ions in solution, so most metallic materials in the flow path can create interference in the detection scheme, as they create background ions.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, and then connect a supply of the selected mobile phase and a selected column to the LC system before operation. In order to be suitable for LC applications, each connection must be able to withstand the typical operating pressures of the LC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections in LC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples, and cannot be routinely used for ion chromatography. For example, the components in a sample may attach themselves to the wall of stainless steel tubing. This presents problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for "biocompatible" or "metal-free" connections through the use of a material that is chemically inert with respect to such "biological" samples and the mobile phase used with such samples, so that ions will not be released by the tubing and thus contaminate the sample.

In many applications using selector/injector valves to direct fluid flows, and in particular in liquid chromatography, the volume of fluids is small. This is particularly true when liquid chromatography is being used as an analytical method as opposed to a preparative method. Such methods often use capillary columns and are generally referred to as capillary chromatography. In capillary chromatography, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

As noted, liquid chromatography (as well as other analytical) systems typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the LC column itself; and a detector that analyzes the carrier fluid as it leaves the column. Ion chromatography may also utilize a suppressor column to facilitate detection dynamic range. These various components may typically be connected by a miniature fluid conduit, or tubing, such as metallic or polymeric tubing (for ion chromatography), usually having an internal diameter of 0.003 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. In addition, the use of such approaches to connect components of an LC system often results in deformation or swaging of a ferrule used to provide a leak proof seal of tubing to a fitting or component. This often means that the ferrule and tubing connection, once made, cannot be reused without a risk of introducing dead volumes into the system. In addition, such approaches may involve crushing or deformation of the inner diameter of the tubing, which may adversely affect the flow characteristics and the pressures of the fluid within the tubing.

Another approach to provide a connection in an LC system involves providing a fitting assembly that uses a combination of components, including two separate ferrules. Such an approach is considered undesirable because by requiring two places for the ferrules to provide leak proof seals, it provides two places where the fluid to be analyzed may leak, as well as where dead volumes may be provided. In addition, this approach involves the use of additional components, which can cost more and also increase the time and effect to assemble them to make a connection or disassemble them when disconnecting tubing from a component or other fitting assembly.

There exists a need for fluidic fittings that are more reliable and have increased performance, which can be accomplished by applying a specific amount of torque to a fluidic fitting. The long used standard of "finger tight" when applying torque introduces a great deal of variation into the process. This results in fittings being under tightened, which causes leaks, or potentially over-tightened (with a tool), which can result in damage to fittings and ports. In general a torque limiting fitting would be preferred over the use a torque tool (such as a torque wrench) since torque tools require specific designs to allow access to specific fittings, employee training, additional assembly time, and associated costs (e.g., tool purchase and periodic calibration). Preferably a torque limiting fitting would look and feel like a standard fitting, but reliably and accurately assemble to the correct torque without influence from the user. It would also be required to disassemble like a standard fitting as well.

U.S. Pat. No. 5,183,140 discloses a general torque limiting mechanism, which comprises two rotatable members, one of which is the driving member and the other of which is the driven member. One of the members includes a single radial projection extending from a central hub that engages a recessed area on the other member. Below the torque limit the projection engages the recessed area and allows the driving member to drive the driven member, but above the torque limit the projection disengages the recessed area and prohibits the driving member from driving the driven member. U.S. Pat. No. 7,984,933 discloses a torque limiting fitting, which also comprises two rotatable members, one of which is the driving member and the other of which is the driven member. One of the members includes a lever extending from a central hub that engages an abutment on the other member. Below the torque limit the lever engages the abutment and allows the driving member to drive the driven member, but above the torque limit the lever deflects from the abutment and prohibits the driving member from driving the driven member. However the radial projection and the lever are only supported on one end, which can result in inconsistency in the torque limit and generally lower maximum torque values.

It will be understood by those skilled in the art that, as used herein, the term "LC system" is intended in its broad sense to include all apparatus and components in a system used in connection with a liquid chromatography system, and that the discussion of fittings in the context of LC systems is exemplary, as the invention may apply beyond LC systems to gas and ion chromatography, as well as or in vitro diagnostic or environmental analysis, and in other analytical instruments and systems, and may be made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Although the following discussion focuses on liquid chromatography, those skilled in the art will appreciate that much of what is said with respect to LC systems also has application to other types of AI systems and methods.

Therefore, it is an object of the present invention to provide a torque limited fitting for use in an LC or other AI system.

It is another object of the present invention to provide a torque limited fitting that can be reusable about 5 to 10 times or more.

It is another object of the present invention to provide a torque limited fitting that performs like a regular fitting.

It is another object of the present invention to provide a mechanism allowing an operator to quickly disconnect or connect tubing or other component of an LC or other AI system.

It is another object of the present invention to provide a mechanism to reduce inefficiency and wasted time in connecting or disconnecting tubing or other component of an LC or other AI system.

It is yet another object of the present invention to provide a mechanism to allow an operator to quickly replace tubing or other component of an LC or other AI system.

It is yet another object of the present invention to provide a mechanism to allow an operator to quickly and easily achieve a leak-free connection of tubing or other component of an LC or other AI system by hand.

It is still another object of the present invention to provide a torque limited fitting to minimize the risk of leakage or damage to the tubing of an LC system.

It is still another object of the present invention to provide a biocompatible torque limited fitting to allow an operator to quickly and easily achieve a biocompatible connection of tubing or other component of an LC or other AI system.

It is still another object of the present invention to provide a "metal-free" torque limited fitting to allow an operator to quickly and easily achieve a metal-free connection of tubing or other component of an LC or other AI system.

The above and other advantages of the present invention will become readily apparent to those skilled in the art from the following detailed description of the present invention, and from the attached drawings, which are briefly described below.

SUMMARY OF THE INVENTION

The present disclosure overcomes one or more of the deficiencies of the prior art by providing torque limiting fittings that are well-suited for use in liquid chromatography and other analytical instrument systems.

The present disclosure provides a torque limited fitting for use in an analytical instrument system, comprising a head having a first end and a second end and a passageway therethrough, an externally tapered portion proximal to the second end of the head, an inner wall and at least a first internal abutment attached to the inner wall, and a body having a first end, a second end, a head with an outer wall and an inner wall and comprising at least a first external abutment, an external lip proximal to the head of the body, an external threaded portion, and a passageway therethrough, wherein the external lip of the body is adapted to securely engage with the external tapered portion of the head. The head can comprise a plurality of internal abutments and/or a plurality of external splines. Alternatively the head portion of the body can comprise a plurality of external abutments. In certain embodiments the head portion of the body can comprise an opening with a side wall instead of slots. The body can also comprise a first external non-tapered portion, a first external tapered portion and a second external non-tapered portion between the head of the body and the external lip and/or a third external non-tapered portion, a second external tapered portion and a fourth external non-tapered portion between the external lip and the external threaded portion. The angle of the external tapered portion of the head and/or the angle of the first external tapered portion of the body can be about 60° included angle. The angle of the second external tapered portion of the body can be about 90° included angle. In certain aspects the head and/or the body can comprise polyetheretherketone. The fitting can also include at least one tube extending through the internal passageway of the body, and the analytical instrument system can comprise a liquid chromatography, gas chromatography, ion chromatography, in vitro diagnostic analysis or environmental analysis system.

The present disclosure also provides an analytical instrument system comprising at least one torque limited fitting comprising a head having a first end and a second end and a passageway therethrough, an externally tapered portion proximal to the second end of the head, an inner wall and at least a first internal abutment attached to the inner wall, and a body having a first end, a second end, a head comprising at least a first external abutment and defining at least a first slot, the at least a first external abutment of the body proximal to the slot, an external lip proximal to the head of the body, an external threaded portion, and a passageway therethrough, wherein the external lip of the body is adapted to securely engage with the external tapered portion of the head. The analytical instrument system can also comprise a ferrule comprising an internal passageway located proximal the second end of the body of the torque limited fitting, and can further comprise at least one tube extending through the internal passageway of the body and the internal passageway of the ferrule. The analytical instrument system can comprise a liquid chromatography, gas chromatography, ion chromatography, an in vitro diagnostic analysis or environmental analysis system.

The present disclosure further provides a method of connecting tubing in an analytical instrument system comprising connecting a torque limited fitting and a ferrule comprising a tube extending therethrough to a port, fitting or component of the analytical instrument system; wherein the torque limited fitting comprises a head having a first end and a second end and a passageway therethrough, an externally tapered portion proximal to the second end of the head, an inner wall and at least a first internal abutment attached to the inner wall, and a body having a first end, a second end, a head comprising at least a first external abutment and defining at least a first slot, at least a first external abutment of the body proximal to the slot, an external lip proximal to the head of the body, an external threaded portion, and a passageway therethrough, wherein the external lip of the body is adapted to securely engage with the external tapered portion of the head, wherein the port, fitting or component comprises an internal threaded portion, and wherein the internal threaded portion of the port, fitting or component is adapted to securely engage with the external threaded portion of the body. The analytical instrument system can comprise a liquid chromatography, gas chromatography, ion chromatography, in vitro diagnostic analysis or environmental analysis system.

In the presently disclosed torque limiting fittings the abutments on the head portion of the body are attached to a portion of the outer wall that is supported on both ends. This design is non-obvious compared to prior art torque limiting fitting designs which utilize projections that are only supported on one end (a lever). The present design is also superior to prior art torque limiting fitting designs, wherein the use of a lever that is only supported on one end can result in a higher incidence of breakage, inconsistent torque limits and generally lower maximum torque values.

These and other embodiments and advantages of the disclosed torque limited fittings are described below.

BRIEF DESCRIPTION OF THE DRAWINGS

The following drawings are included to further demonstrate certain aspects and embodiments of the present invention. The invention may be better understood by reference to one or more of these drawings in combination with the detailed description of specific embodiments presented herein.

FIG. 19. An exploded side view of various components of an alternative embodiment of a torque limited fitting in accordance with one aspect of the present invention.

FIG. 20. An exploded perspective view of the torque limited fitting of FIG. 2.

FIG. 21A, FIG. 21B and FIG. 21C. Views of an embodiment of the head portion of the torque limited fitting of FIG. 19. FIG. 21A. A side view of the head portion of the torque limited fitting of FIG. 19. FIG. 21B. Cross-sectional view of the head portion of the torque limited fitting of FIG. 19. FIG. 21C. Top view of the head portion of the torque limited fitting of FIG. 19.

FIG. 22A, FIG. 22B and FIG. 22C. Views of an embodiment of the body portion of the torque limited fitting of FIG. 19. FIG. 22A. A side view of the body portion of the torque limited fitting of FIG. 19. FIG. 22B. Cross-sectional view of the body portion of the torque limited fitting of FIG. 19. FIG. 22C. Top view of the body portion of the torque limited fitting of FIG. 19.

DETAILED DESCRIPTION

Figure 1:
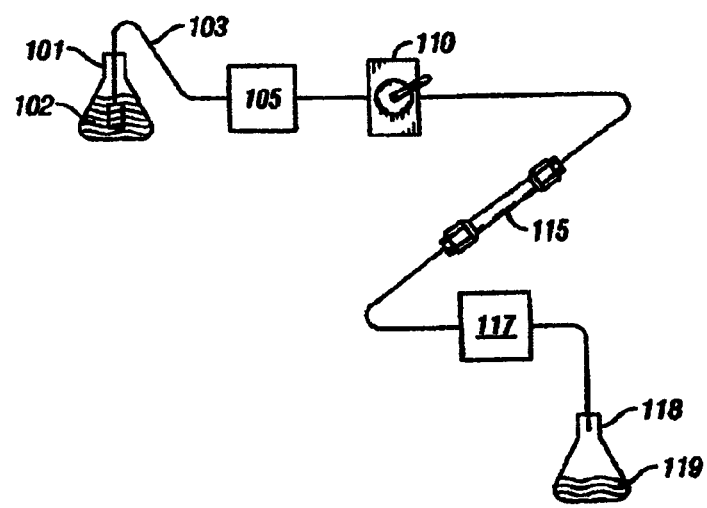
FIG. 1. A block diagram of a conventional liquid chromatography system.

In FIG. 1, a block diagram of the essential elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well-known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system, other analytical systems can be used in connection with various embodiments of the invention, such as a mass spectrometry, microflow chromatography, nanoflow chromatography, nano-scale liquid chromatography, capillary electrophoresis, or reverse-phase gradient chromatography system. Indeed, it is believed that a fitting assembly according to at least some embodiments may be used in a wide variety of applications, including any application involving fluid flow and connections.

Preferably, for an LC system to be biocompatible, the various components (except where otherwise noted) that may come into contact with the effluent or sample to be analyzed are made of the synthetic polymer polyetheretherketone, which is commercially available under the trademark PEEK™ from VICTREX®. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
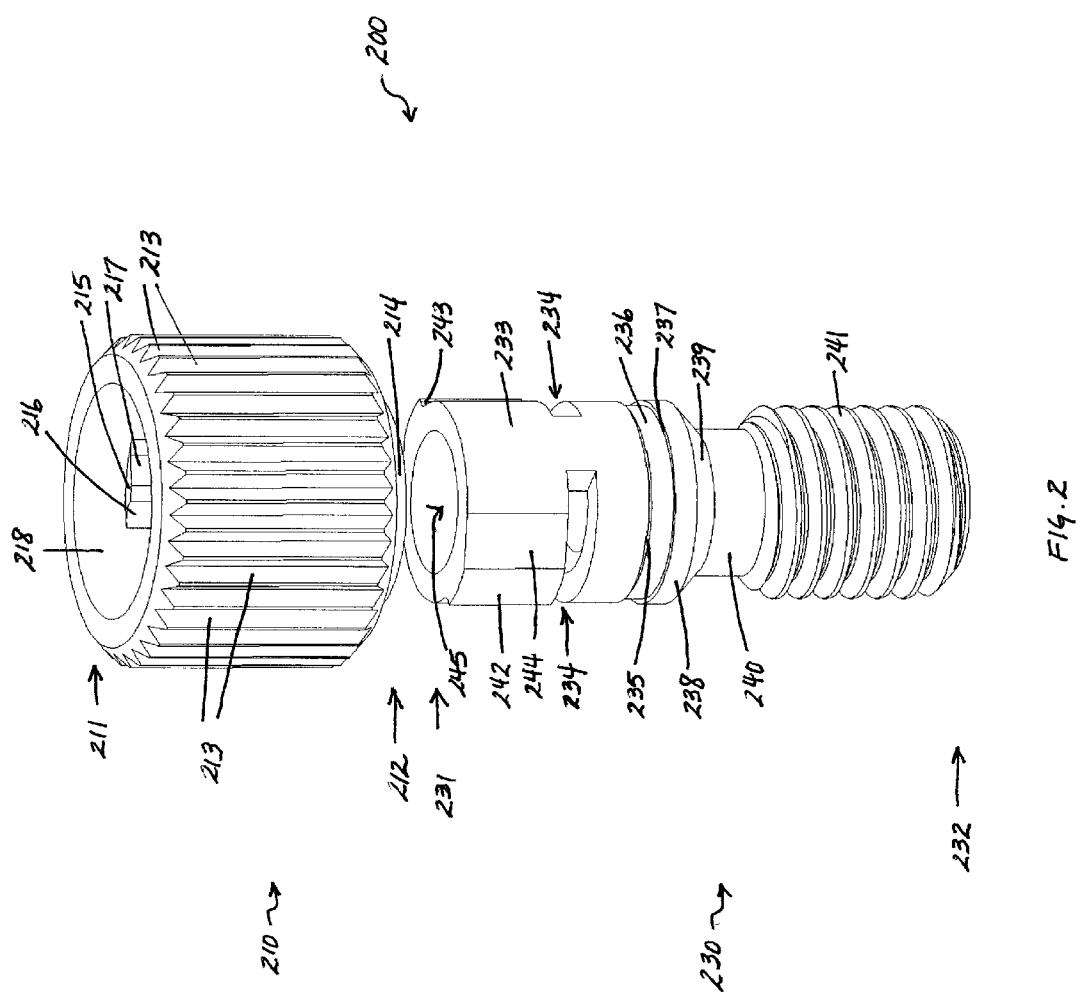
FIG. 2. An exploded perspective view of various components of an embodiment of a torque limited fitting in accordance with one aspect of the present invention.

Referring now to FIG. 2, a first embodiment of a torque limited fitting 200 is shown. Like features and elements in the drawings have the same numerals in the various figures. As shown in FIG. 2, the torque limited fitting 200 includes a head portion 210 and a body portion 230. Body portion 230 has a smaller profile than body portion 530 (detailed below), which may be important in certain applications. Thus it is believed that body portion 230 provides greater flexibility without an increase in manufacturing complexity or cost. Head 210 comprises a first end 211, a second end 212, external splines 213, an external generally tapered portion 214 proximal the second end 212 of the head 210, and abutment 215 having a first ramped portion 216 and a second ramped portion 217 on inner wall 218. Body 230 comprises first end 231, second end 232, head portion 233 defining slots 234 and comprising abutments 242 having a first ramped portion 243 and a second ramped portion 244, first external generally tapered portion 235, first external essentially non-tapered portion 236, external lip 237, second external essentially non-tapered portion 238, second external generally tapered portion 239, third external essentially non-tapered portion 240 and external threaded portion 241, and defines passageway 245. As shown in FIG. 2, head 210 and body 230 are generally circular and symmetric about a center axis. Those skilled in the art will realize that a circular shape has advantages, but the outer diameters in particular of head 210 may have a non-circular shape if desired, such as having flat or concave surface portions, to allow an operator to more easily grip and rotate head 210. In addition, although a plurality of splines 213 are shown on head 210 in FIG. 2, the number and presence of such splines are optional. As detailed herein, the externally threaded portion 241 of the body 230 may be adapted to be removably secured to a corresponding threaded portion of a port, a fitting, or a component of an LC or other analytical instrument (AI) system (not shown). Those skilled in the art will appreciate that the externally threaded portion 241 of the body 230 may be adapted so that it can be removably engaged with any sized port, fitting, or component of an LC or other AI system (not shown). The use of external threads on one element, such as the body 230, versus internal threads, is a matter of selection. Those skilled in the art will therefore appreciate that the body 230 in an alternative embodiment could have internal threads (not shown) located near a second end that could be engaged with external threads (not shown) located near the first end of an alternative embodiment of a port, fitting, or component of an LC or AI system (not shown).

Still referring to FIG. 2, it can be seen that the first ramped portion 216 of abutment 215 of head 210 is steeper than the second ramped portion 217 of abutment 215 of head 210, and similarly that the first ramped portion 243 of abutment 242 of body 230 is steeper than the second ramped portion 244 of abutment 242 of body 230. This difference allows the fitting to be tightened to the desired torque via engagement of the second ramped portion 217 of the abutment 215 of head 210 and second ramped portion 244 of abutment 242 of body 230, and then released (which in general requires greater torque than used to tighten the fitting) via engagement of the steeper first ramped portion 216 of abutment 215 of head 210 and the steeper first ramped portion 243 of abutment 242 of body 230. In addition, the first external tapered portion 235 and second external tapered portion 239 of the body 230 each form a truncated conical shape. As shown in FIG. 2, the first external generally tapered portion 235 and second external generally tapered portion 239 of the body 230 each define an angle from the axis of the body 230. However, those skilled in the art will appreciate that the first external generally tapered portion 235 and second external generally tapered portion 239 of the body 230 can define a different angle if desired, and can define angles that are about equal to each other, or differ from each other, depending upon the particular application. As detailed herein, upon assembly of the head 210 and the body 230 the external generally tapered portion 214 of the head 210 is adapted to be received proximal to the first external essentially non-tapered portion 236 of the body 230, and the external lip 237 of the body 230 is adapted to engage the external generally tapered portion 214 of the head to prevent separation of the head 210 and the body 230 under normal operating conditions (not shown in FIG. 2; see FIG. 11 through FIG. 14).

It will be appreciated that the head 210 and body 230 can comprise a number of different materials, and specific materials or combinations of specific materials may be selected, together with or in place of, the selected shape and size of the features of head 210 and body 230, to obtain desired minimum and maximum torque values. For example, head 210 and/or body 230 in torque limited fitting 200 can comprise a metal, such as stainless steel, or can comprise a different material, such as a polymer, or combinations thereof. For example, the torque limited fitting 200 can comprise a head 210 and body 230 that both comprise a polymer, such as polyetheretherketone (PEEK), or the head 210 and/or the body 230 can comprise stainless steel. It will be appreciated that a variety of metals and polymers may be selected for either head 210 or body 230 depending on the particular application, as that may involve a particular type of sample, a particular type of solvent, and/or a particular pressure range. Polymers that can be used in the manufacture of the head 210 and body 230 include, but are not limited to, high performance or commodity grade plastics, PEEK, polyphenylene sulfide (PPS), perfluoroalkoxy (PFA), polyoxymethylene (POM; sold commercially as DELRIN®), TEFLON®, TEFZEL®, polypropylene and ethylene tetrafluoroethylene (ETFE), and combinations thereof. In addition, PEEK (or other polymers) may be used that is reinforced with carbon, carbon fibers, glass fibers, or steel fibers, or the like. Additionally, the selection of materials for the tubing, such as fluorinated ethylene propylene (FEP), perfluoroalkoxy (PFA), PEEK, PEEKsil™, PPS, ETFE, ethylene chlorotrifluoroethylene (ECTFE), stainless steel, or fused silica, may lead to a selection of a particular material for head 210 and/or body 230. Those skilled in the art will further appreciate that torque limited fitting 200 is shown as a fitting connection for connecting tubing to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

In certain applications utilizing PEEK, the PEEK used in fabrication of the head 210, body 230, and/or tubing (not shown in FIG. 2, see FIG. 13 and FIG. 14) may be annealed according to manufacturer's recommendations. In general, the PEEK is ramped from about 70° F. to between about 300° F. and about 320° F. over about 40 to about 60 minutes, held at about 300° F. to about 320° F. for about 150 to about 180 minutes, ramped from between about 300° F. and about 320° F. to between about 392° F. and about 560° F. over about 90 minutes to about 300 minutes, held between about 392° F. and about 560° F. for between about 240 minutes and about 2880 minutes, and ramped down to between about 70° F. and about 284° F. over about 360 minutes to about 600 minutes. However, the skilled artisan will readily understand that different annealing protocols may be used in other applications.

In order for a fitting assembly to seal, it should generally remain in compression (relative to the surface of the port) throughout all environmental conditions. Therefore, in certain aspects a coating with a high coefficient of friction is applied to at least a portion of the internal passageway 245 of body 230 of the described fitting assembly 200. The high coefficient of friction between the outer surface of the tubing and the internal passageway 245 of body 230 keeps the tubing from extruding out of the port during pressurization, which results in increased burst pressure. In such embodiments the fitting connection or assembly 200 is coated at the internal surface of passageway 245 of body 230 that contacts the tubing starting at approximately 0.005 inches, about 0.0075 inches, about 0.01 inches, or about 0.02 inches from the second end 232 of the body 230 of the torque limited fitting 200. Coatings suitable for use with the presently described torque limited fitting include, but are not limited to, nickel, silica carbide, copper, and diamond coatings, and combinations thereof.

Figure 3:
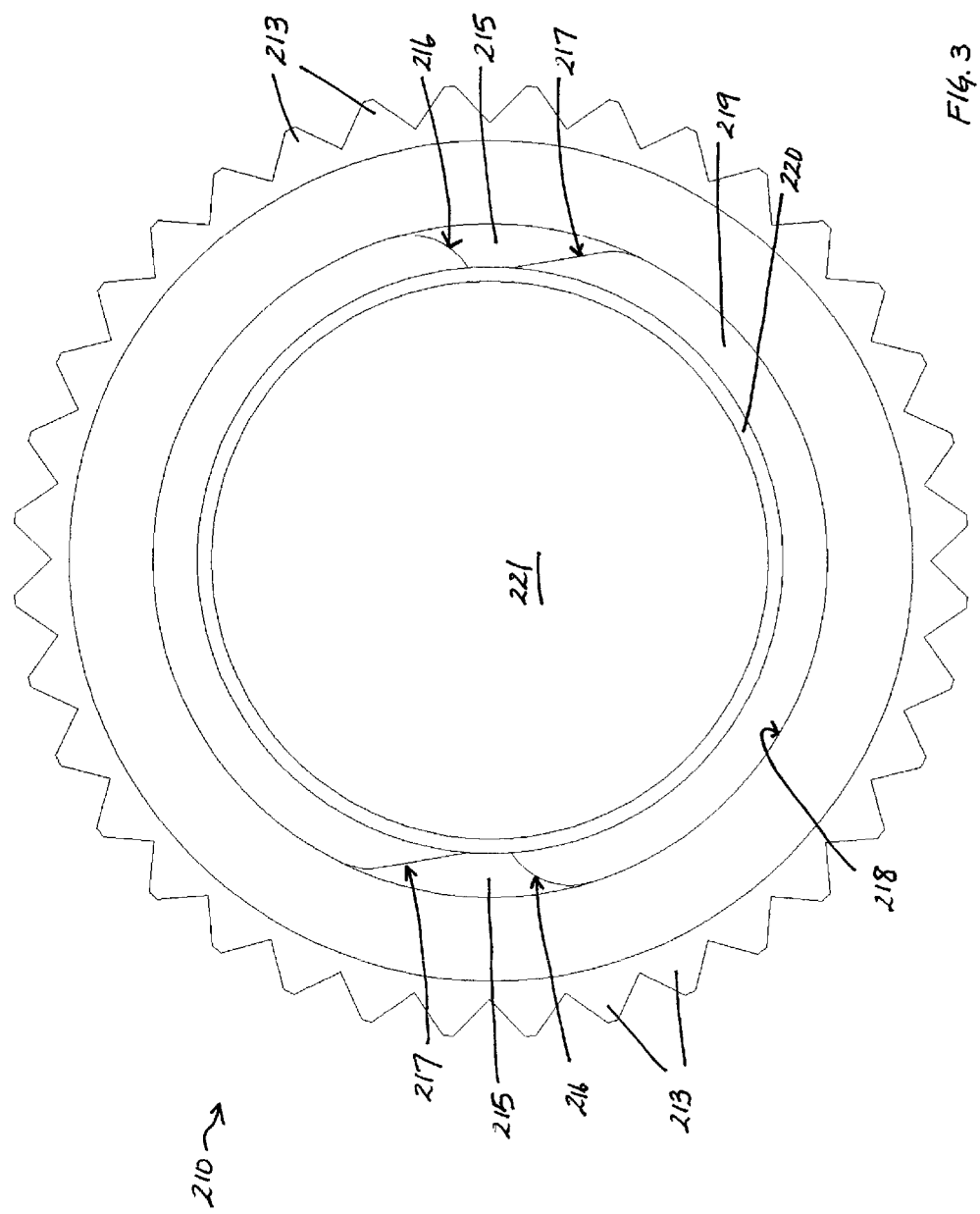
FIG. 3. A top view of the head portion of the torque limited fitting of FIG. 2.
Figure 4:
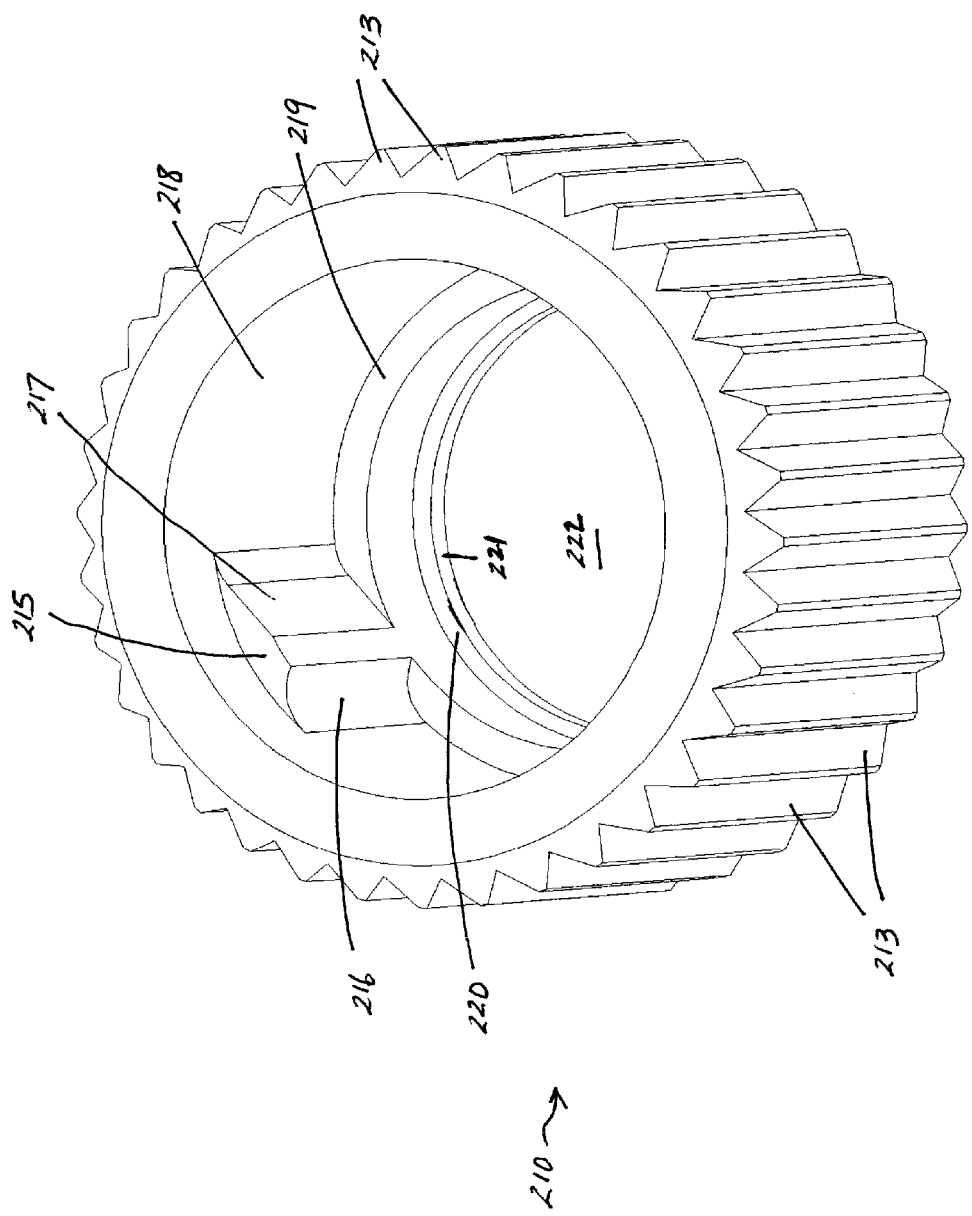
FIG. 4. A front perspective view of the head portion of the torque limited fitting of FIG. 2.
Figure 5:
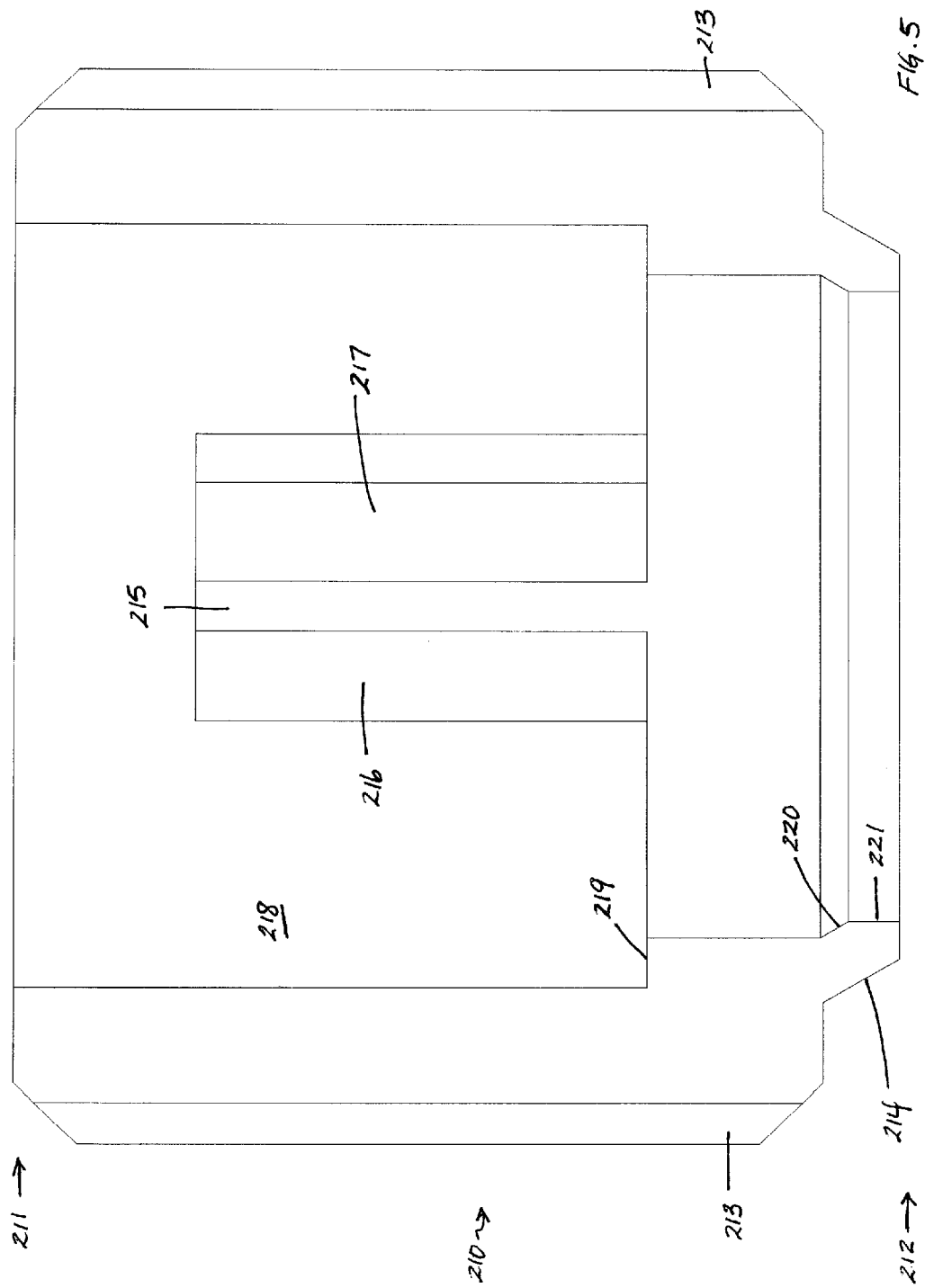
FIG. 5. A cross-sectional view of the head portion of the torque limited fitting of FIG. 2.

FIG. 3, FIG. 4 and FIG. 5 show different views of the head 210 of torque limited fitting 200 shown in FIG. 2. FIG. 3 shows a top view of head 210 having splines 213, abutments 215 having first ramped portion 216 and second ramped portion 217, inner wall 218, base 219, internal generally tapered portion 220 and internal passageway 221. FIG. 4 shows a perspective view of the head 210 comprising splines 213, abutment 215 having first ramped portion 216 and second ramped portion 217, inner wall 218, base 219, internal generally tapered portion 220, internal essentially non-tapered portion 221 and passageway 222. FIG. 5 shows a cross-sectional view of head 210 having first end 211, second end 212, splines 213, abutment 215 having first ramped portion 216 and second ramped portion 217, inner wall 218, base 219, internal generally tapered portion 220 and essentially non-tapered portion 221.

Figure 6:
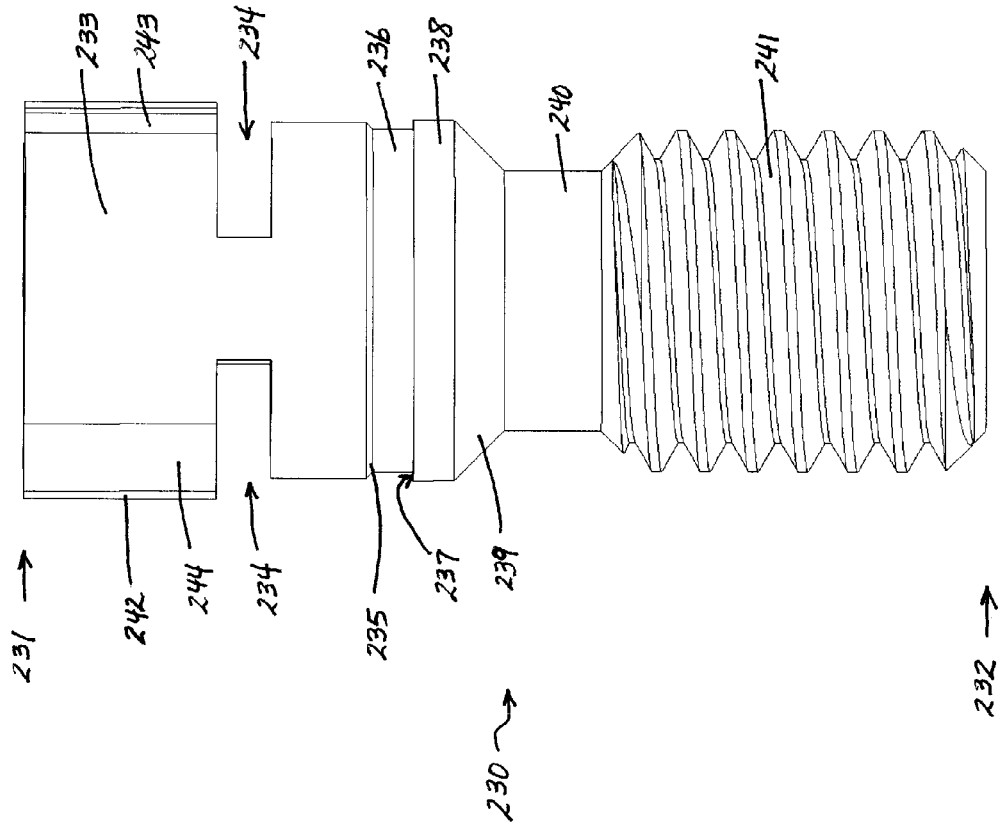
FIG. 6. A side view of the body portion of the torque limited fitting of FIG. 2.
Figure 7:
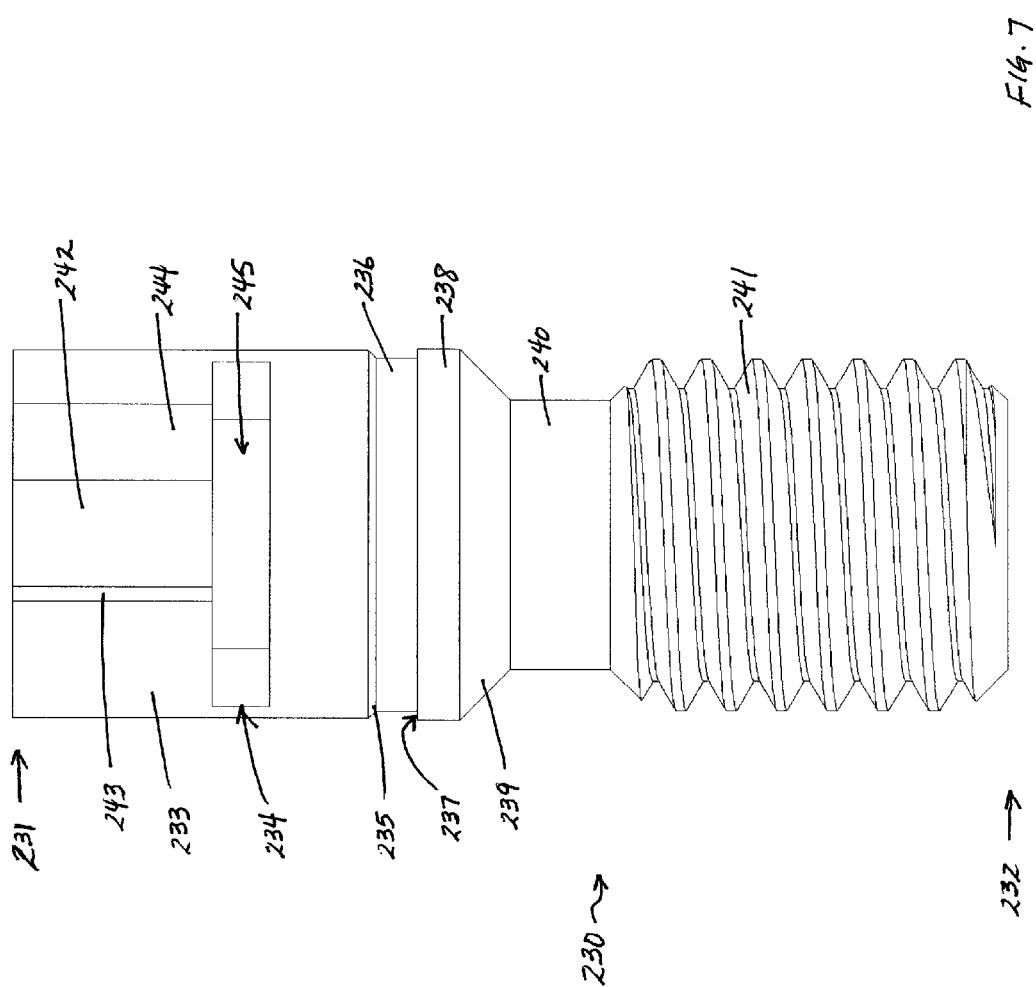
FIG. 7. A front view of the body portion of the torque limited fitting of FIG. 2.
Figure 8:
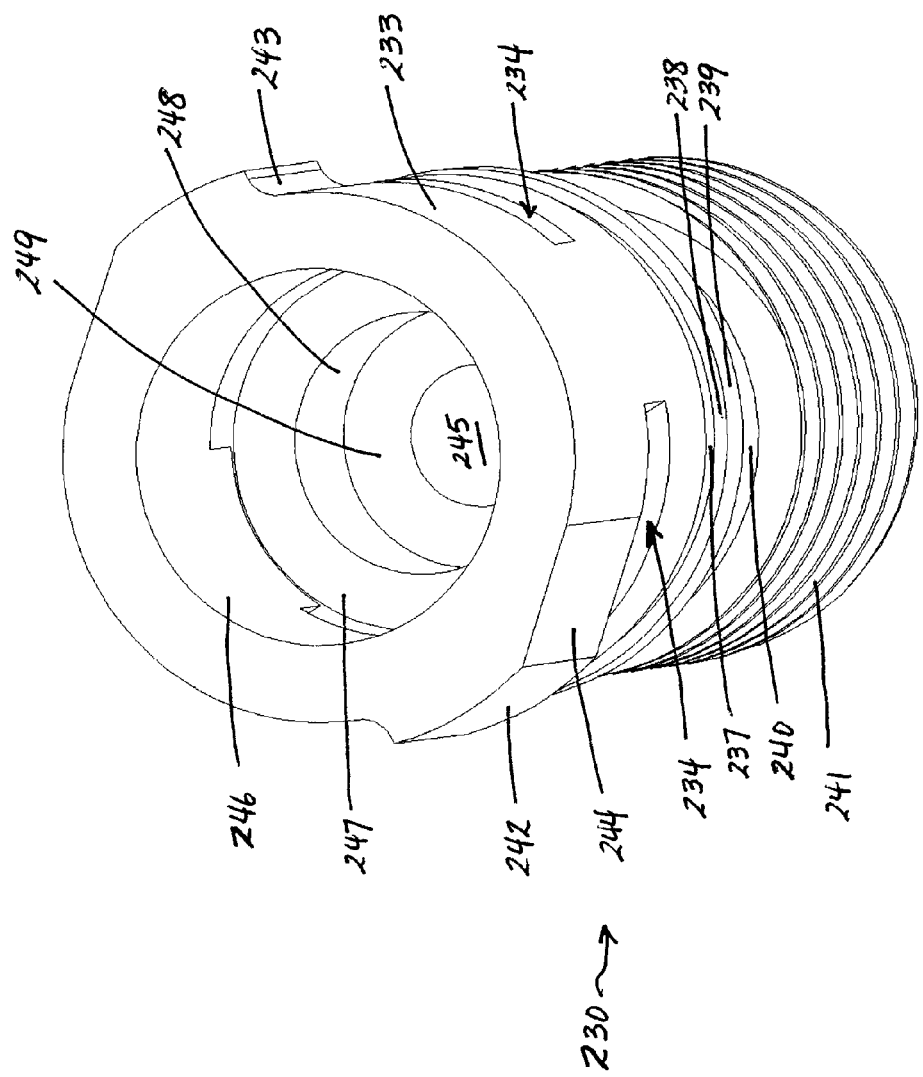
FIG. 8. A top perspective view of the body portion of the torque limited fitting of FIG. 2.

FIG. 6, FIG. 7 and FIG. 8 show different views of the body 230 of torque limited fitting 200 shown in FIG. 2. FIG. 6 shows a side view of body 230 comprising first end 231, second end 232, head portion 233 defining slots 234 and comprising abutments 242 having a first ramped portion 243 and a second ramped portion 244, first external generally tapered portion 235, first external essentially non-tapered portion 236, external lip 237, second external essentially non-tapered portion 238, second external generally tapered portion 239, third external essentially non-tapered portion 240 and external threaded portion 241. FIG. 7 shows a side view of body 230 rotated 90° relative to the view shown in FIG. 3. Once again, body 230 comprised first end 231, second end 232, head portion 233 defining slots 234 and comprising abutments 242 having a first ramped portion 243 and a second ramped portion 244, first external generally tapered portion 235, first external essentially non-tapered portion 236, external lip 237, second external essentially non-tapered portion 238, second external generally tapered portion 239, third external essentially non-tapered portion 240 and external threaded portion 241. FIG. 8 shows a top perspective view of body 230 comprising first end 231, second end 232, head portion 233 defining slots 234 and comprising abutments 242 having a first ramped portion 243 and a second ramped portion 244, external lip 237, second external essentially non-tapered portion 238, second external generally tapered portion 239, third external essentially non-tapered portion 240, external threaded portion 241, inner wall 246, first internal generally tapered portion 247, first internal essentially non-tapered portion 248 and second internal generally tapered portion 249. Passageway 245 through body 230 is also shown. Not visible in FIG. 8 are first external generally tapered portion 235 and first external essentially non-tapered portion 236.

Figure 9:
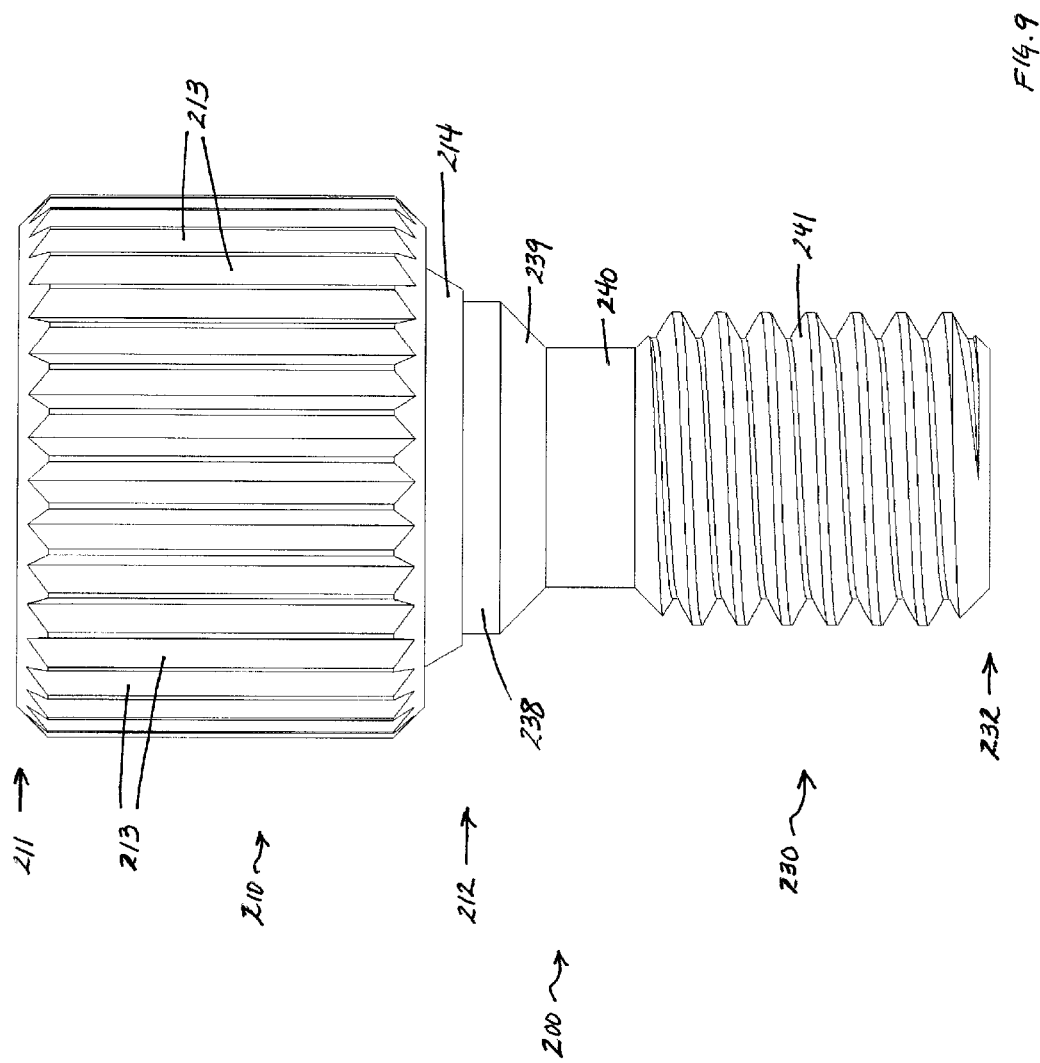
FIG. 9. A side view of the torque limited fitting of FIG. 2 upon assembly.

Referring now to FIG. 9, a side view of torque limited fitting 200 shown in FIG. 2 is depicted upon assembly of head 210 and body 230. Visible on head portion 210 is first end 211, second end 212, external splines 213, and external generally tapered portion 214 proximal the second end 212 of the head 210. Visible on body portion 230 is second external essentially non-tapered portion 238, second external generally tapered portion 239, third external essentially non-tapered portion 240, external threaded portion 241, and second end 232 of body 230.

Figure 10:
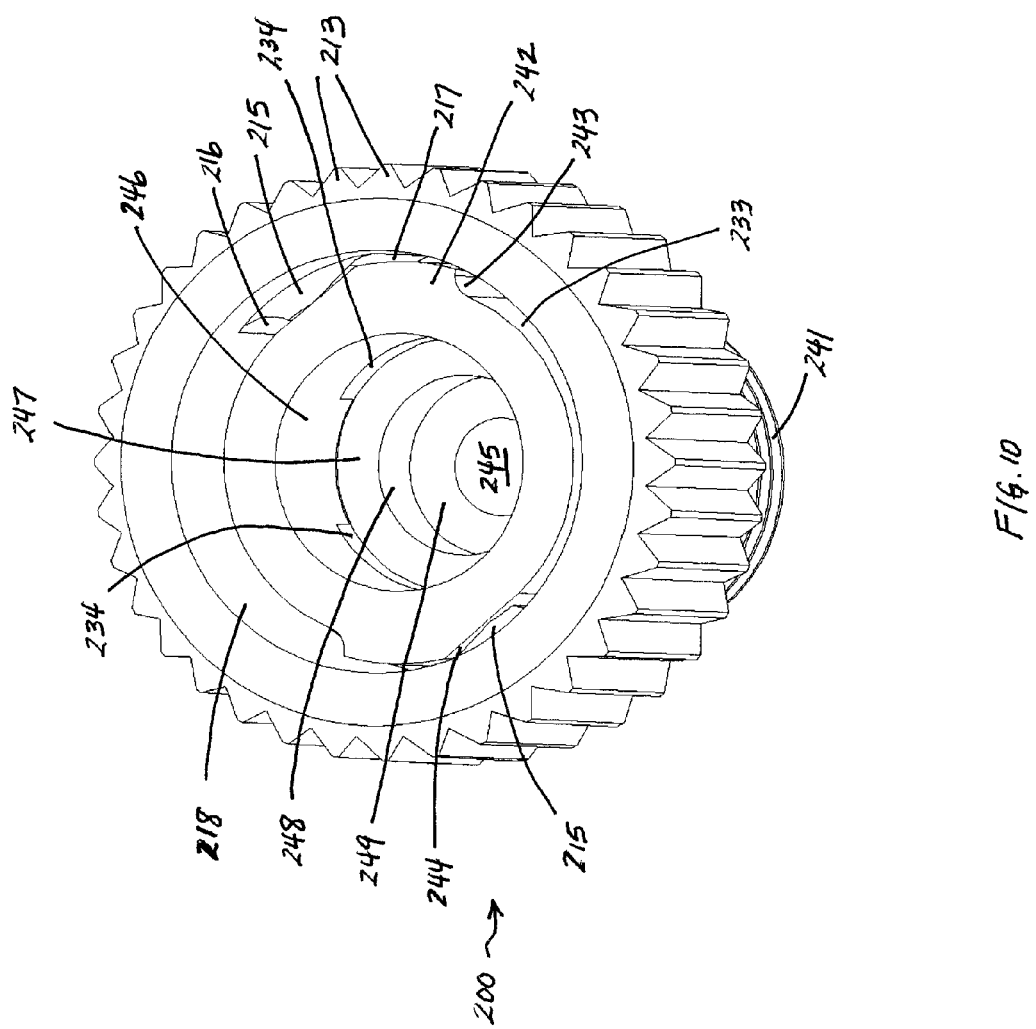
FIG. 10. A top perspective view of the torque limited fitting of FIG. 2 upon assembly.

Referring now to FIG. 10, a perspective top view of torque limited fitting 200 shown in FIG. 2 is depicted upon assembly of head 210 and body 230. Visible on head portion 210 are external splines 213, abutments 215 having first ramped portion 216 and second ramped portion 217, and inner wall 218. Visible on body portion 230 is head portion 233 defining slots 234 and comprising abutments 242 having a first ramped portion 243 and second ramped portion 244, external threaded portion 241, passageway 245, inner wall 246, first internal generally tapered portion 247, first internal essentially non-tapered portion 248 and second internal generally tapered portion 249.

Figure 11:
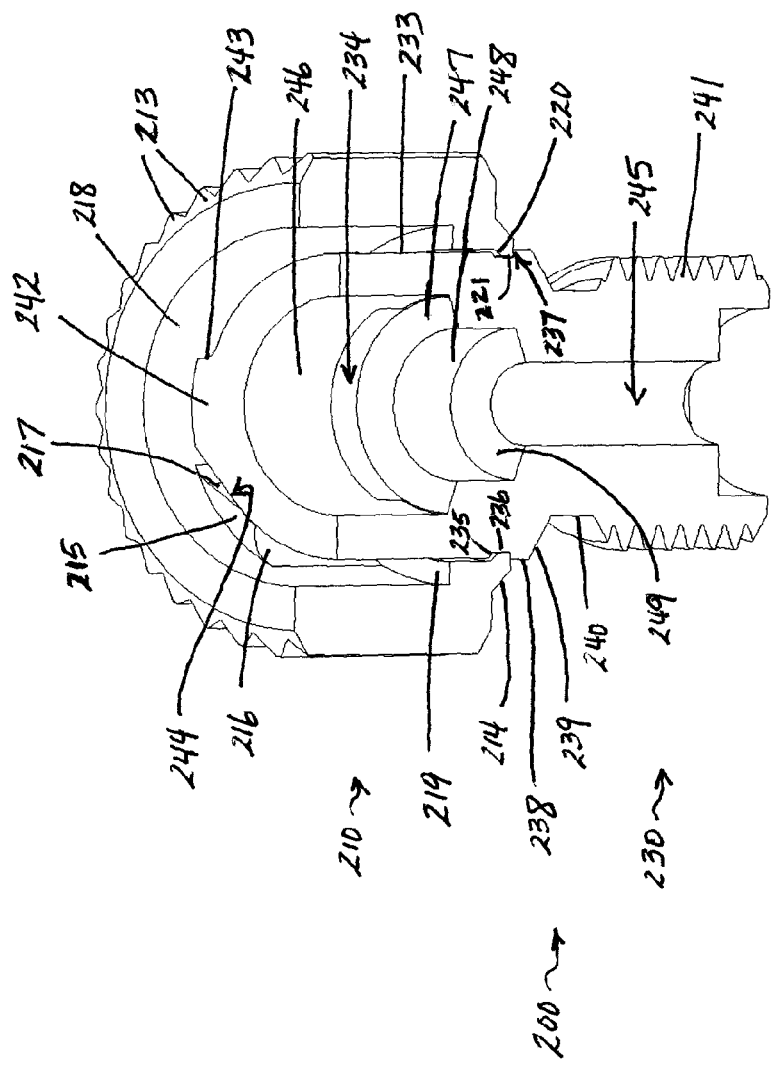
FIG. 11. A front perspective cross-sectional view of the torque limited fitting of FIG. 2 upon assembly.

Referring now to FIG. 11, a side cross-sectional view of torque limited fitting 200 shown in FIG. 2 is depicted upon assembly of head 210 and body 230. Visible on head portion 210 are external splines 213, external generally tapered portion 214 proximal the second end of the head 210, abutment 215 having first ramped portion 216 and second ramped portion 217, inner wall 218, base 219, internal generally tapered portion 220 and internal essentially non-tapered portion 221. Visible on body portion 230 is head portion 233 defining slot 234 and comprising abutment 242 having first ramped portion 243 and second ramped portion 244, first external generally tapered portion 235 and first external essentially non-tapered portion 236, external lip 237, second external essentially non-tapered portion 238, second external generally tapered portion 239, third external essentially non-tapered portion 240, external threaded portion 241, inner wall 246, first internal generally tapered portion 247, first internal essentially non-tapered portion 248, second internal generally tapered portion 249 and passageway 245. As seen in FIG. 11, upon assembly external tapered portion 214 of head 210 engages lip 237 of body 230, which prevents separation of head 210 and body 230 of torque limited fitting 200 during normal operating conditions.

Figure 12:
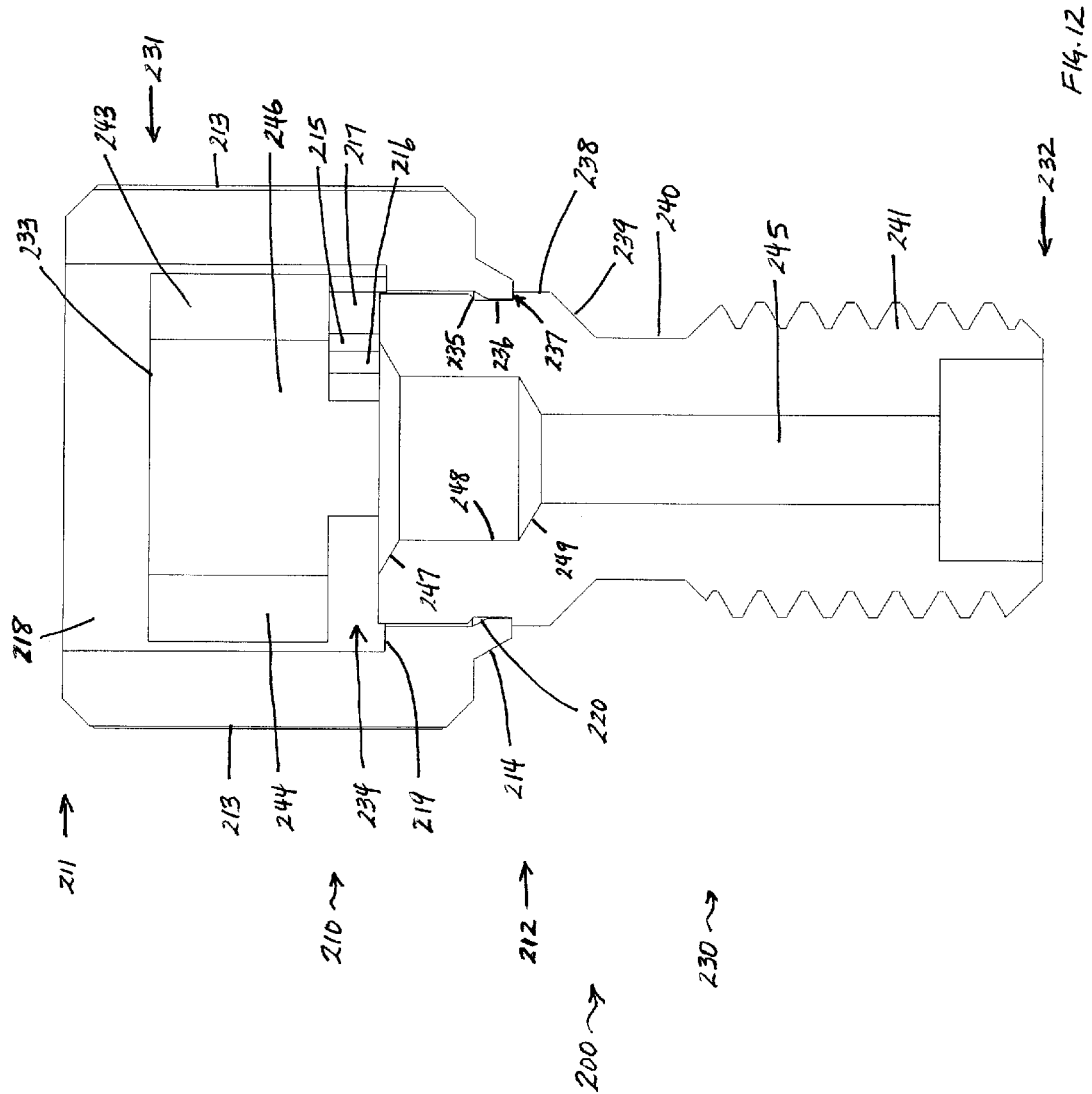
FIG. 12. A cross-sectional view of the torque limited fitting of FIG. 2 upon assembly.

Referring now to FIG. 12, a cross-sectional view of torque limited fitting 200 shown in FIG. 2 is depicted upon assembly of head 210 and body 230. Once again head portion 210 comprises first end 211, second end 212, external splines 213, external generally tapered portion 214 proximal the second end 212 of the head 210, abutment 215 having first ramped portion 216 and second ramped portion 217, inner wall 218, base 219, internal generally tapered portion 220 and internal essentially non-tapered portion 221. Body portion 230 once again comprises first end 231, second end 232, head portion 233 defining slot 234 and comprising abutment 242 having first ramped portion 243 and second ramped portion 244, first external generally tapered portion 235 and first external essentially non-tapered portion 236, external lip 237, second external essentially non-tapered portion 238, second external generally tapered portion 239, third external essentially non-tapered portion 240, external threaded portion 241, inner wall 246, first internal generally tapered portion 247, first internal essentially non-tapered portion 248, second internal generally tapered portion 249 and passageway 245. As seen in FIG. 12, upon assembly external generally tapered portion 214 of head 210 engages lip 237 of body 230, which prevents separation of head 210 and body 230 of torque limited fitting 200 during normal operating conditions.

Figure 13:
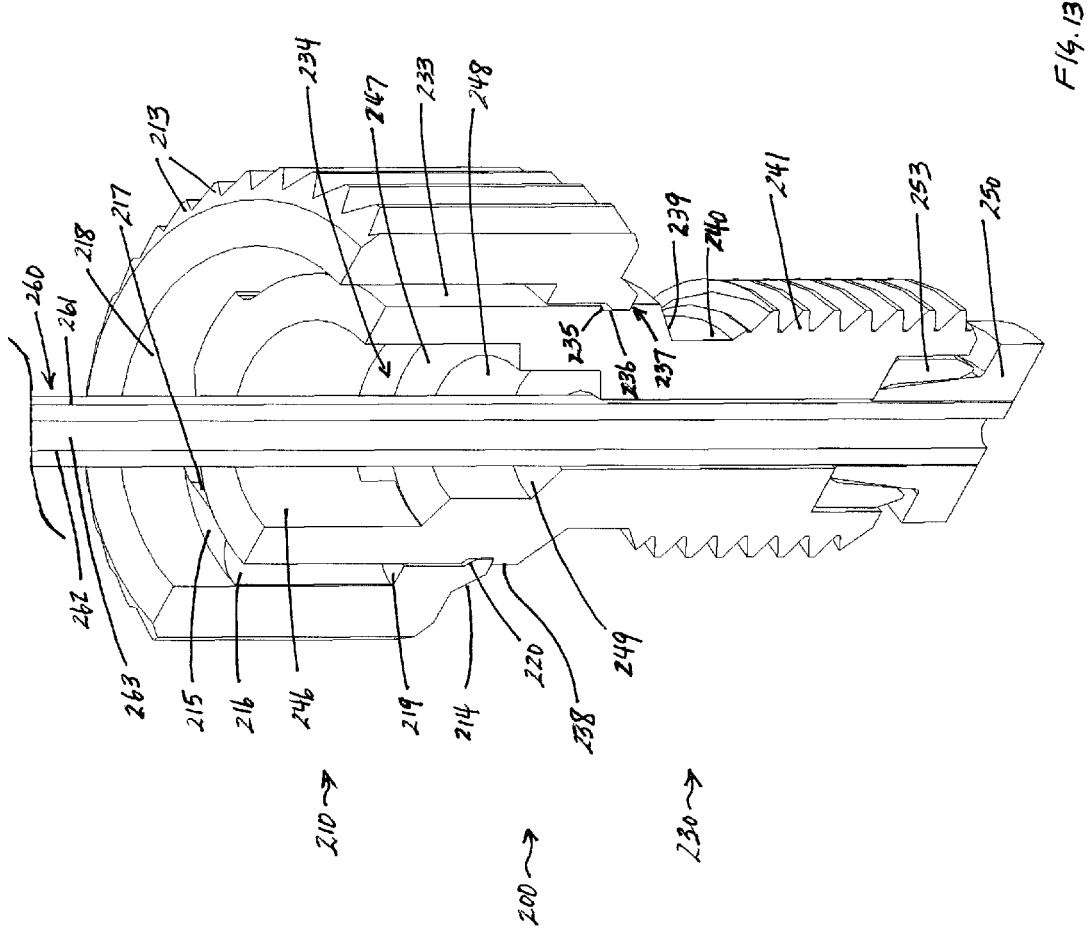
FIG. 13. A cross-sectional view of the torque limited fitting of FIG. 2 upon assembly with tubing, a ferrule and a lock ring.

FIG. 13 shows a side perspective cross-sectional view of the torque limited fitting 200 with head 210 and body 230 shown in FIG. 9 with a piece of tubing 260 placed in the passageway 245 (not visible in FIG. 13) of the body 230 and engaged with ferrule 250 and lock ring 253. As described previously head portion 210 comprises external splines 213, external generally tapered portion 214 proximal the second end 212 of the head 210, abutment 215 having first ramped portion 216 and second ramped portion 217, inner wall 218, base 219, internal generally tapered portion 220 and internal essentially non-tapered portion 221. Body portion 230 once again comprises head portion 233 defining slot 234 and comprising abutment 242 having first ramped portion 243 and second ramped portion 244, first external generally tapered portion 235 and first external essentially non-tapered portion 236, external lip 237, second external essentially non-tapered portion 238, second external generally tapered portion 239, third external essentially non-tapered portion 240, external threaded portion 241, inner wall 246, first internal generally tapered portion 247, first internal essentially non-tapered portion 248 and second internal generally tapered portion 249. Ferrule 250 and lock ring 253 each comprise a passageway (not visible in FIG. 13). Tubing 260 comprises outer wall 261, inner wall 262 and passageway 263. Upon assembly external generally tapered portion 214 of head 210 acts to keep head 210 and body 230 engaged through interaction with lip 237 of body 230. Torque limited fitting 200 is engaged in port (not shown) through interaction of the external threaded portion 241 of body 230 of torque limited fitting 200 and the internal threaded portion (not shown) of the port (not shown), with the ferrule 250 and tubing 260 held flush against face (not shown) of the port (not shown).

Figure 14:
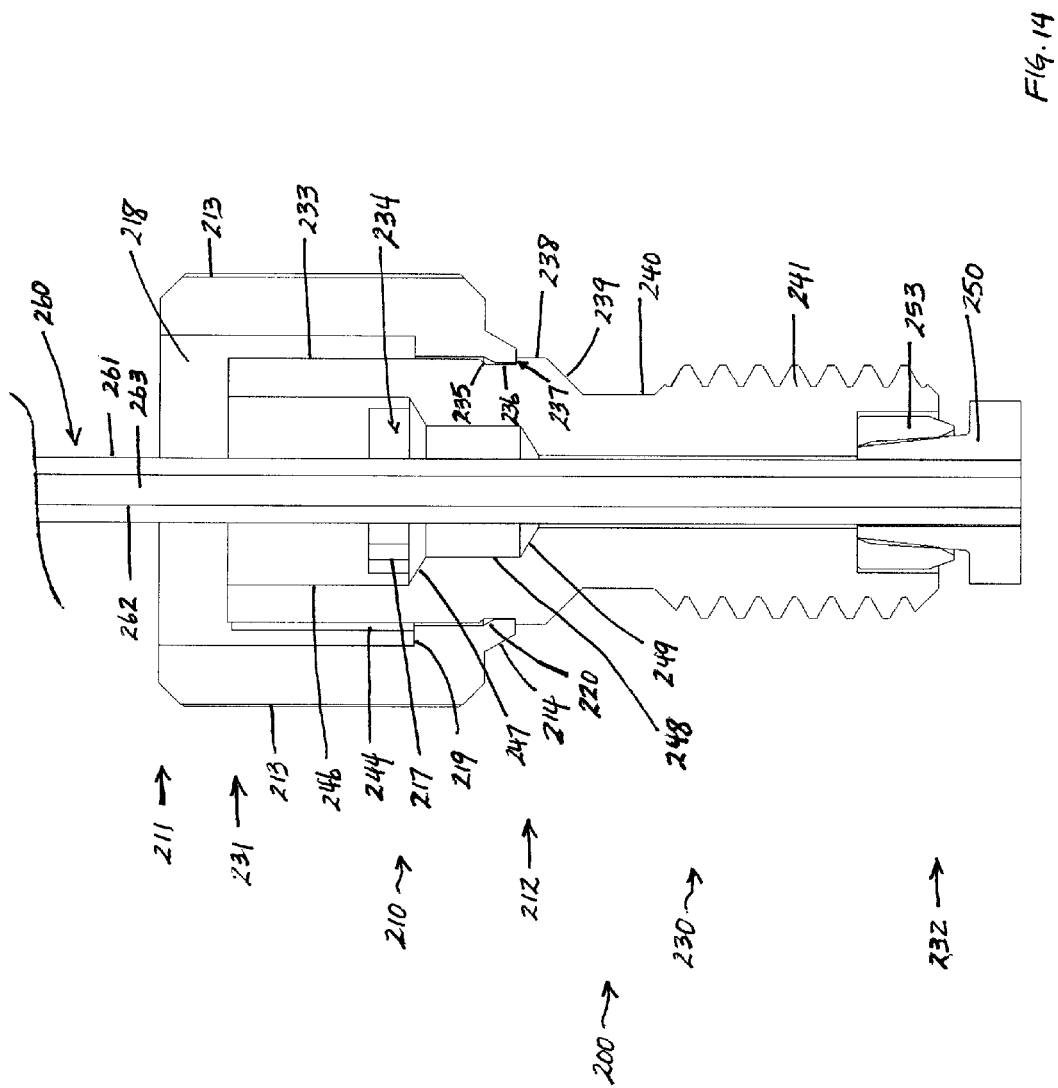
FIG. 14. A side cross-sectional view of the torque limited fitting of FIG. 2 upon assembly with tubing, a ferrule and a lock ring.

FIG. 14 shows a cross-sectional view of the torque limited fitting 200 with head 210 and body 230 shown in FIG. 9 with a piece of tubing 260 placed in the passageway 245 (not visible in FIG. 14) of the body 230 and engaged with ferrule 250 and adapter ring 253. As described previously head portion 210 comprises first end 211, second end 212, external splines 213, external generally tapered portion 214 proximal the second end 212 of the head 210, abutment 215 having first ramped portion 216 and second ramped portion 217, inner wall 218, base 219, internal generally tapered portion 220 and internal essentially non-tapered portion 221. Body portion 230 once again comprises first end 231, second end 232, head portion 233 defining slot 234 and comprising abutment 242 having first ramped portion 243 and second ramped portion 244, first external generally tapered portion 235 and first external essentially non-tapered portion 236, external lip 237, second external essentially non-tapered portion 238, second external generally tapered portion 239, third external essentially non-tapered portion 240, external threaded portion 241, inner wall 246, first internal generally tapered portion 247, first internal essentially non-tapered portion 248 and second internal generally tapered portion 249. Ferrule 250 comprises and adapter ring 253 each comprise a passageway (not visible in FIG. 14). Tubing 260 comprises outer wall 261, inner wall 262 and passageway 263. Upon assembly external generally tapered portion 214 of head 210 acts to keep head 210 and body 230 engaged through interaction with lip 237 of body 230. Torque limited fitting 200 is engaged in port (not shown) through interaction of the external threaded portion 241 of body 230 of torque limited fitting 200 and the internal threaded portion (not shown) of the port (not shown), with the ferrule 250 and tubing 260 held flush against face (not shown) of the port (not shown).

As shown in FIG. 5, the externally tapered portion 214 of the head 210 has an outer diameter and an inner diameter as defined by the non-tapered portion 221, with the outer diameter greater than the inner diameter. Although the outer diameter varies along the externally tapered portion 214 due to the taper, the outer diameter at all points along the externally tapered portion 214 is nonetheless greater than the inner diameter of the externally tapered portion 214 of the head 210. In addition, the internal tapered portion 220 defines an inner diameter of the head 210 that is greater than the inner diameter defined by the non-tapered portion of head 210. As shown in FIG. 12 (for example), the head 210 and body 230 are secured together. In FIG. 12, the first essentially non-tapered portion of body 230 is generally surrounded by the non-tapered portion 221 of the head 210. Moreover, the outer diameter of the second essentially non-tapered portion of the body 230 is greater than the inner diameter of the externally tapered portion 214 defined by the non-tapered portion 221 of the head 210. As also shown in FIG. 12, at least a portion of the first end 231 of the body 230 fits within a portion of head 210; this portion of the first end 231 of the body 230 has a greater outer diameter than the inner diameter of the externally tapered portion 214 of the head 210 as defined by non-tapered portion 221 of the head 210.

Functionally, when the head 210 is rotated, the abutments 242 on the head portion 233 of the body 230 interfere with the abutments 215 on the inner wall 218 of the head 210. This interference allows torque to be transferred to the external threaded portion 241 of the body 230, which engages an internal threaded portion in a fluidic port (not shown). This in turn creates an axial force on the ferrule 250 at the external threaded portion 241 proximal the second end 232 of the body 230. When a predetermined torque value is reached, each abutment 242 on the head portion 233 of the body 230 is forced radially into the center of the body 230 (this action acts like a spring, similar to a leaf spring in a car). This deflection allows the abutments 215 on the inner wall 216 of the head 210 to snap over, and therefore not allow a higher torque to be transferred to the external threaded portion 241 of the body 230 and the ferrule 250.

Generally, the rotational force or torque applied to connect to the torque limited fitting 200, ferrule 250, and tubing 260 extending therethrough to a port (or fitting, or other component in an LC or AI system, not shown) accomplishes two major tasks. First, the force of the connection of the fitting 200 and ferrule 250 needs to be sufficient to provide a sealed and leak proof connection to the port (or fitting or other LC or AI system component, not shown). In addition, the force of the connection of the fitting 200 and ferrule 250 needs to be sufficient so that the tubing 260 is securely held and is sufficient to prevent detachment due to the hydraulic force created from the fluid pressure on the wetted end of the tubing 260. It is believed that the latter function typically involves greater forces than the former. It is believed that the fitting 200 provides an advantage in that it allows for the use of a predetermined maximum torque to provide better connections.

Methods of using the torque limited fitting 200 are now described in further detail. Torque limited fitting 200 can be provided to the operator with the head 210 and the body 230 pre-assembled, although in alternate embodiments the operator can assemble the fitting 200 by connecting the head 210 and the body 230. In one approach, the operator can insert a portion of the tubing through the passageway 245 of the pre-assembled head 210 and body 230 and a ferrule 250. The operator can then engage the externally threaded portion 241 of the body 230 with the internally threaded portion of a port (or fitting or other component of a LC or AI system, not shown). Once the externally threaded portion 241 of the body 230 and the internally threaded portion of the port (or fitting or other component of a LC or AI system, not shown) begin to mate or engage, the operator then rotates the head 210 of the fitting 200 relative to the port (or fitting or other component of a LC or AI system, not shown), rotates the port (or fitting or other component of a LC or AI system, not shown) relative to the head 210 of the fitting 200, or rotates both the head 210 of the fitting 200 and the port (or fitting or other component of a LC or AI system, not shown) relative to each other. By so rotating the head 210 of the fitting 200 and the port (or fitting or other component of a LC or AI system, not shown) relative to one another, the operator drives the externally threaded portion 241 proximal the second end of the body 230 against the ferrule 250. In doing so, the second end 252 of the ferrule 250 is compressed and held firmly against the face of the port (not shown), thereby forming a leak-proof connection. Because the maximum torque of the torque limited fitting 200 is predetermined based on the specific design of the fitting 200, a leak-proof connection may be obtained by the operator without the use of additional tools such as a wrench, torque wrench, pliers or the like.

To disconnect a fitting 200, an operator may either rotate the fitting 200 relative to the port (or fitting or other component of a LC or AI system, not shown) in the opposite direction used to connect the fitting 200 to the port (not shown), rotate the port (or fitting or other component of a LC or AI system, not shown) relative to the fitting assembly 200 in the opposite direction used to connect the fitting 200 to the port (not shown), or rotate both the port (or fitting or other component of a LC or AI system, not shown) and the fitting assembly 200 relative to each other in the opposite direction used to connect the fitting 200 to the port (not shown). By rotating the port (or fitting or other component of a LC or AI system, not shown) and/or the fitting assembly 200 relative to one another in the opposite direction used to connect the fitting 200 to the port (not shown), the operator thus rotates the externally threaded portion 241 of body 230 and the internally threaded portion of the port (or fitting or other component of a LC or AI system, not shown), respectively, and thereby disengages the connection between such threaded portions. At this point, the operator can use the assembly 200 and the leak-proof connection it provides, until the operator decides to remove the tubing 260 from the assembly 200. By selecting the direction of the threading of the externally threaded portion 241 of the body 230 and internally threaded portion of the port (or fitting or other component of a LC or AI system, not shown), respectively, the operator can turn the entire fitting 200 (when connected) by turning or rotating head 210, such that the fitting 200 rotates relative to the port (or fitting or other component of a LC or AI system, not shown) and disengages therefrom. Thus, the fitting 200 is easily disconnected from the port (or fitting or other component of a LC or AI system, not shown).

Figure 15:
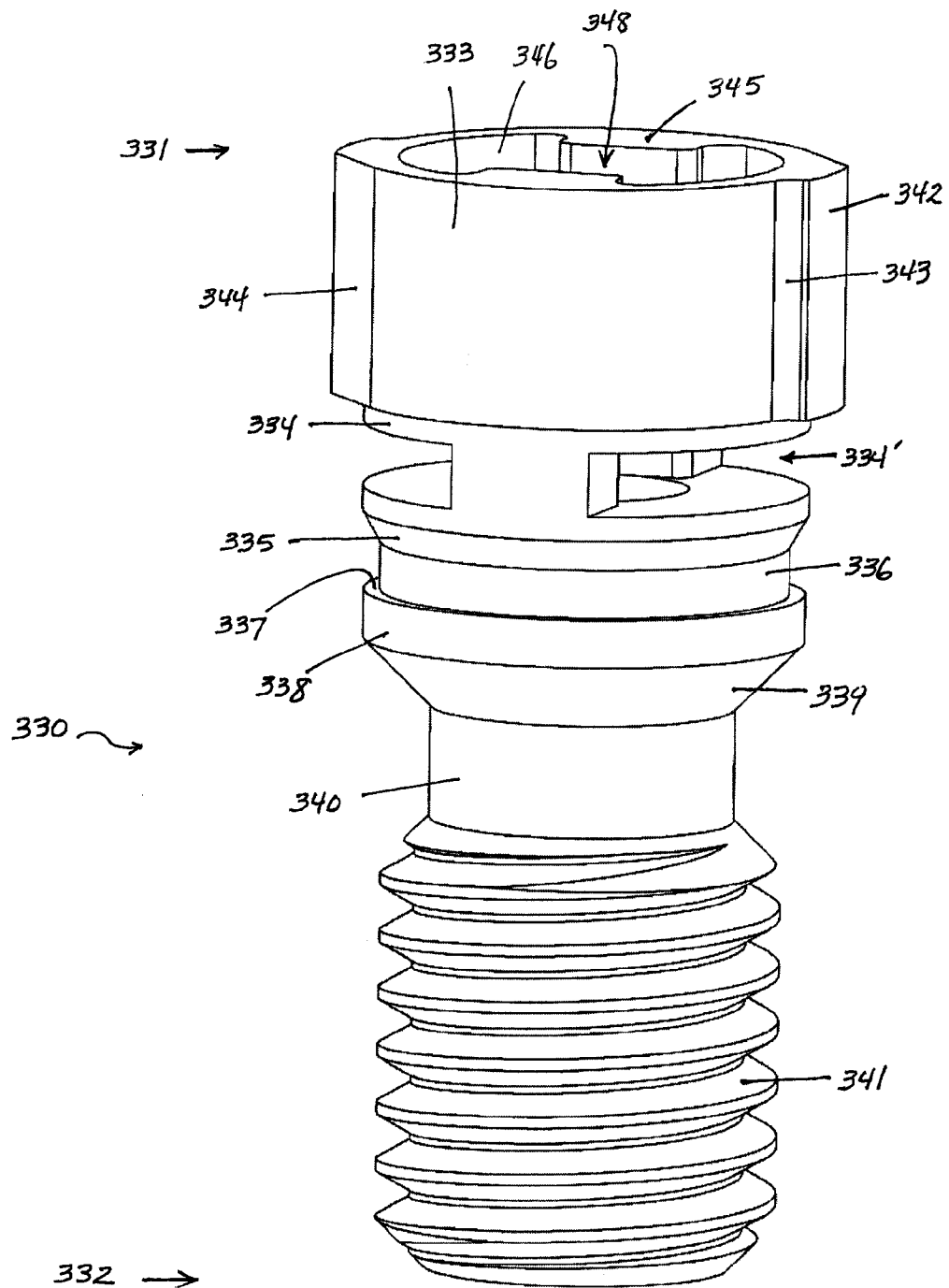
FIG. 15. Side perspective view of an alternative embodiment of a body portion of a torque limiting fitting in accordance with one aspect of the present invention.

Referring now to FIG. 15, an alternative embodiment of a body portion 330 of a torque limited fitting is shown. Body portion 330 comprises first end 331, second end 332, head portion 333, first external essentially non-tapered portion 334 defining slots 334', first external generally tapered portion 335, second external essentially non-tapered portion 336, external lip 337, third external essentially non-tapered portion 338, second external generally tapered portion 339, fourth external essentially non-tapered portion 340, external threaded portion 341, abutment 342 having a first ramped portion 343 and a second ramped portion 344, protrusion 345, inner wall 346 and passageway 348. As shown in FIG. 15, body 330 is generally circular and symmetric about a center axis. Once again, the externally threaded portion 341 of the body 330 may be adapted to be removably secured to a corresponding threaded portion of a port, a fitting, or a component of an LC or other analytical instrument (AI) system (not shown). Those skilled in the art will appreciate that the externally threaded portion 341 of the body 330 may be adapted so that it can be removably engaged with any sized port, fitting, or component of an LC or other AI system (not shown). The use of external threads on one element, such as the body 330, versus internal threads, is a matter of selection. Those skilled in the art will therefore appreciate that the body 330 in an alternative embodiment could have internal threads (not shown) located near a second end that could be engaged with external threads (not shown) located near the first end of an alternative embodiment of a port, fitting, or component of an LC or AI system (not shown).

Still referring to FIG. 15, it can be seen that the first external generally tapered portion 335 and second external generally tapered portion 339 of the body 330 each form a truncated conical shape. As shown in FIG. 15, the first external generally tapered portion 335 and second external generally tapered portion 339 of the body 330 each define an angle from the axis of the body 330. However, those skilled in the art will appreciate that the first external generally tapered portion 335 and second external generally tapered portion 339 of the body 330 can define a different angle if desired, and can define angles that are about equal to each other, or differ from each other, depending upon the particular application. As detailed herein, upon assembly (not shown in FIG. 15) of the head 210 (see FIG. 2) and the body 330 the external generally tapered portion 214 of the head 210 is adapted to be received proximal to the second external essentially non-tapered portion 336 of the body 330, and the external lip 337 of the body 330 is adapted to engage the external generally tapered portion 214 of the head 210 to prevent separation of the head 210 and the body 330 under normal operating conditions.

Figure 16:
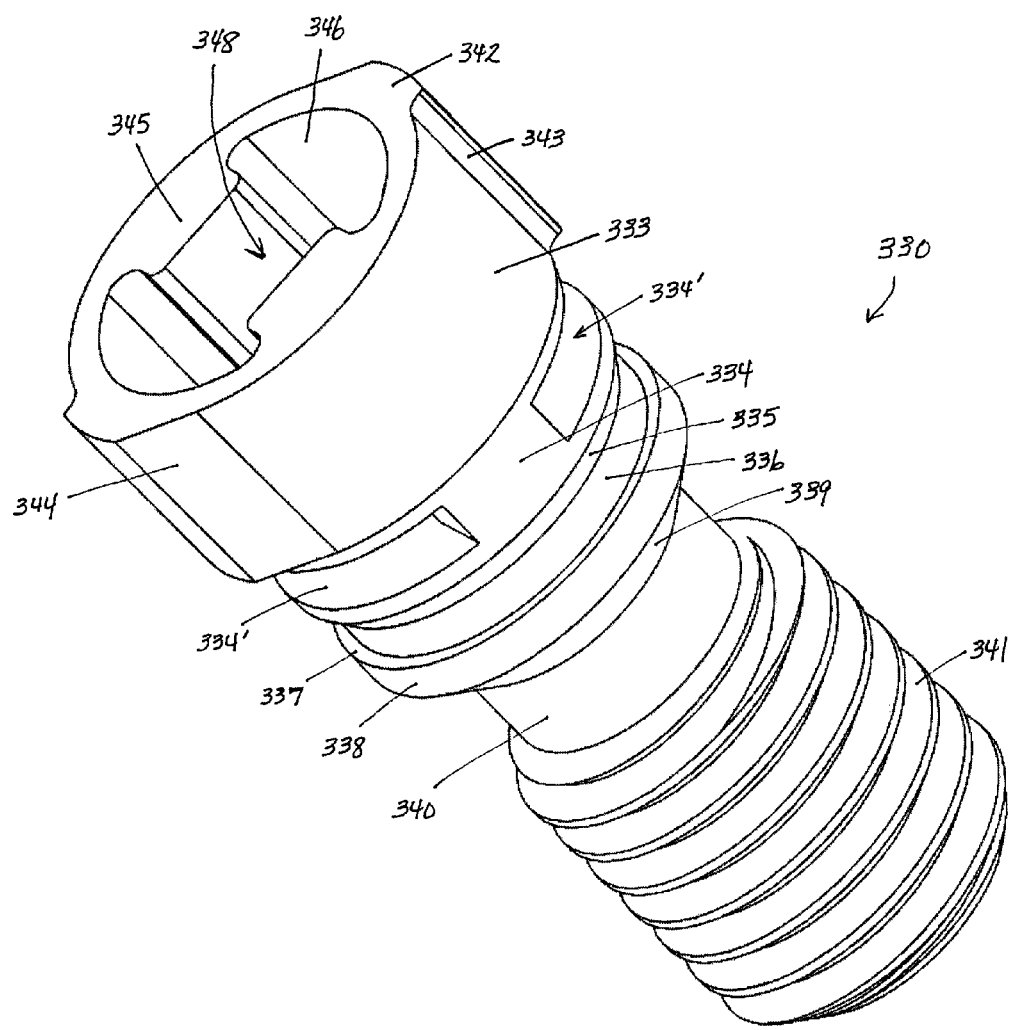
FIG. 16. Perspective view of the alternative embodiment of a body portion of a torque limiting fitting shown in FIG. 15.

FIG. 16 shows a perspective view of the body portion 330 of the torque limited fitting shown in FIG. 15. Once again body 330 includes head portion 333, first external essentially non-tapered portion 334 defining slots 334', first external generally tapered portion 335, second external essentially non-tapered portion 336, external lip 337, third external essentially non-tapered portion 338, second external generally tapered portion 339, fourth external essentially non-tapered portion 340, external threaded portion 341, abutment 342 having a first ramped portion 342 and a second ramped portion 344, protrusion 345, inner wall 346 and passageway 348. As shown in FIG. 16 body 330 includes two abutments 342 located approximately 90° from the protrusions. However, those skilled in the art will appreciate that in alternative embodiments (not shown) body 330 can have one or more abutments 342, which can be located proximal any position along the head portion 333.

Figure 17:
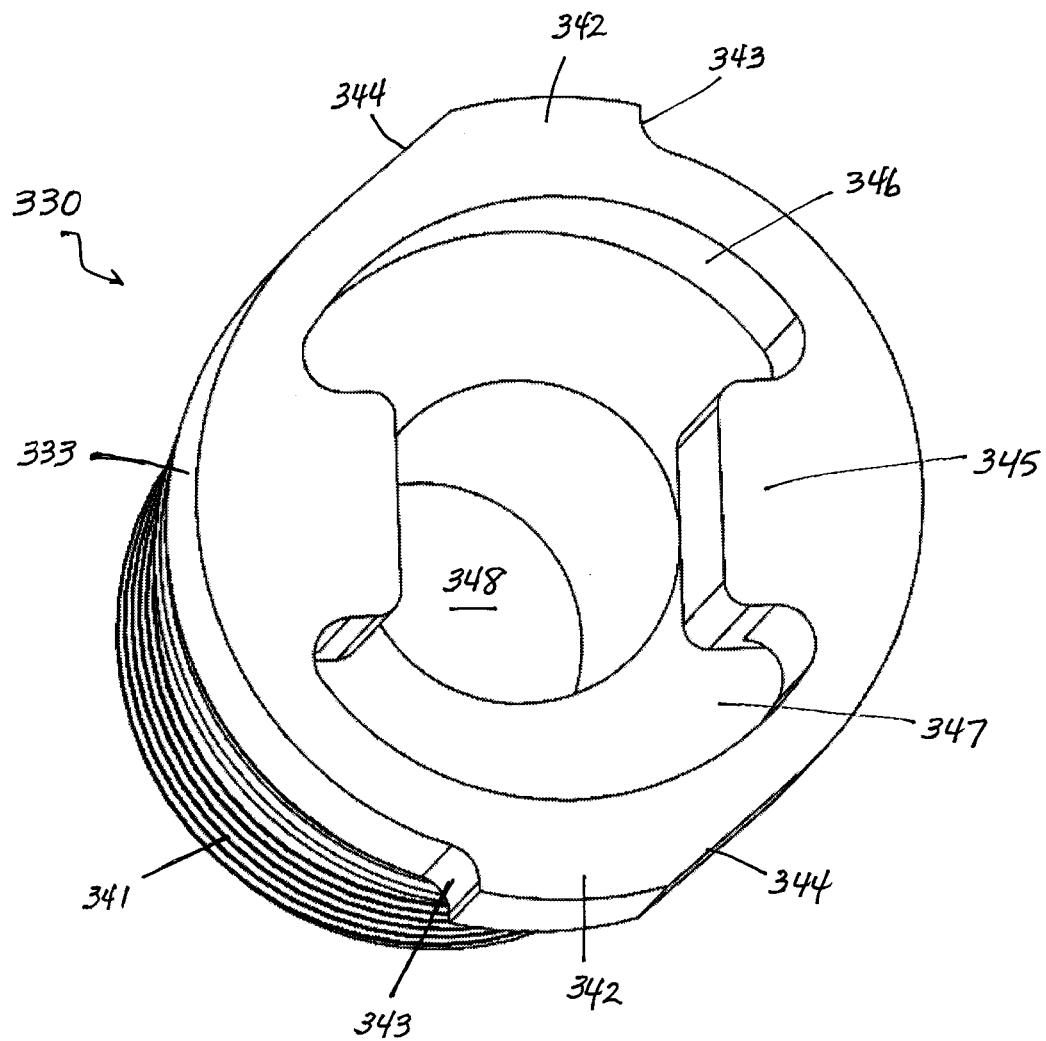
FIG. 17. Top perspective view of the alternative embodiment of a body portion of a torque limiting fitting shown in FIG. 15.

FIG. 17 shows a top perspective view of the body portion 330 of the torque limited fitting shown in FIG. 15. Visible in FIG. 17 are head portion 333, external threaded portion 341, abutments 342 having a first ramped portion 343 and a second ramped portion 344, protrusions 345, inner wall 346, base 347 and internal passageway 348.

Figure 18:
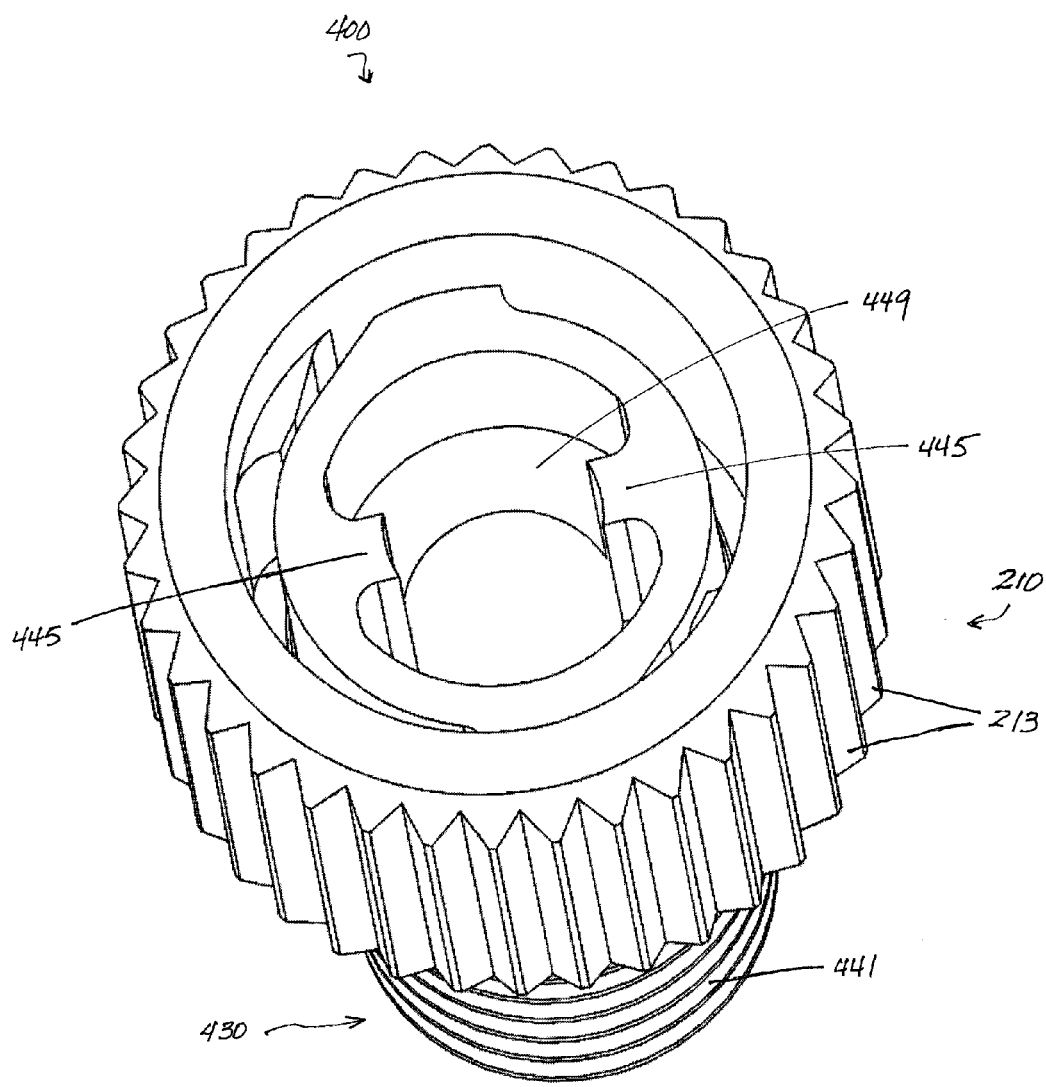
FIG. 18. Top perspective view of an alternative embodiment of a body portion of a torque limiting fitting in accordance with one aspect of the present invention upon assembly with the head portion shown in FIG. 2.

FIG. 18 shows a top perspective view another embodiment of a body portion 430 upon assembly with head portion 210 of the torque limited fitting shown in FIG. 2. Body portion 430 differs from body portion 330 shown in FIG. 15 through FIG. 17 via addition of a bridging element 449 attached to one of protrusions 445.

Referring now to FIG. 19, another embodiment of a torque limited fitting 500 is shown. As shown in FIG. 19, the torque limited fitting 500 includes a head portion 510 and a body portion 530. Head 510 comprises a first end 511, a second end 512, external splines 513, and an external generally tapered portion 514 proximal the second end 512 of the head 510. Body 530 comprises first end 531, second end 532, head portion 533 comprising abutment 542 having a first ramped portion 542' and a second ramped portion 542", first external essentially non-tapered portion 534, first external generally tapered portion 535, second external essentially non-tapered portion 536, external lip 237, third external essentially non-tapered portion 538, second external generally tapered portion 539, fourth external essentially non-tapered portion 540 and external threaded portion 541. As shown in FIG. 19, head 210 and body 230 are generally circular and symmetric about a center axis. Those skilled in the art will realize that a circular shape has advantages, but the outer diameters in particular of head 510 may have a non-circular shape if desired, such as having flat or concave surface portions, to allow an operator to more easily grip and rotate head 510. In addition, although a plurality of splines 513 are shown on head 510 in FIG. 19, the number and presence of such splines are optional. As detailed herein, the externally threaded portion 541 of the body 530 may be adapted to be removably secured to a corresponding threaded portion of a port, a fitting, or a component of an LC or other analytical instrument (AI) system (not shown). Those skilled in the art will appreciate that the externally threaded portion 541 of the body 530 may be adapted so that it can be removably engaged with any sized port, fitting, or component of an LC or other AI system (not shown). The use of external threads on one element, such as the body 530, versus internal threads, is a matter of selection. Those skilled in the art will therefore appreciate that the body 530 in an alternative embodiment could have internal threads (not shown) located near a second end that could be engaged with external threads (not shown) located near the first end of an alternative embodiment of a port, fitting, or component of an LC or AI system (not shown).

Still referring to FIG. 19, it can be seen that the first external generally tapered portion 535 and second external generally tapered portion 539 of the body 530 each form a truncated conical shape. As shown in FIG. 19, the first external generally tapered portion 535 and second external generally tapered portion 539 of the body 530 each define an angle from the axis of the body 530. However, those skilled in the art will appreciate that the first external generally tapered portion 535 and second external generally tapered portion 539 of the body 530 can define a different angle if desired, and can define angles that are about equal to each other, or differ from each other, depending upon the particular application. As detailed herein, upon assembly of the head 510 and the body 530 the external generally tapered portion 514 of the head 510 is adapted to be received proximal to the second external essentially non-tapered portion 536 of the body 530, and the external lip 537 of the body 530 is adapted to engage the external generally tapered portion 514 of the head 510 to prevent separation of the head 510 and the body 530 under normal operating conditions (not shown in FIG. 19; see FIG. 23).

FIG. 20 shows an exploded perspective view of the torque limited fitting 500 shown in FIG. 19. Once again torque limited fitting 500 includes head 510 including splines 513, and body 530 including head portion 533, third external essentially non-tapered portion 538, fourth external essentially non-tapered portion 540 and external threaded portion 541. Visible in FIG. 20 is an internal portion of head portion 510, showing abutment 515 having a first ramped portion 515' and a second ramped portion 515" located on inner wall 516 of head 510, proximal base 517, and internal generally tapered portion 518, which corresponds to the external generally tapered portion 514 (not visible in FIG. 20) of head 510. Also visible in FIG. 20 is a view of the top of head portion 533 of body 530, showing abutments 542 having first ramped portion 542' and second ramped portion 542", which are generally located proximal the center of slots 543, internal tapered portion 544 and internal passageway 545. As shown in FIG. 20 body 530 includes three abutments 542 and three slots 543. However, those skilled in the art will appreciate that in alternative embodiments (not shown) body 530 can have one or more abutments 542 and slots 543. In further embodiments (not shown) the abutments 542 can be located proximal any position along the slots 543.

FIG. 21A, FIG. 21B and FIG. 21C show different views of the head 510 of torque limited fitting 500 shown in FIG. 19 and FIG. 20. FIG. 21A shows a side view of head 510 having a first end 511, a second end 512, external splines 513, and an external generally tapered portion 514 proximal the second end 512 of the head 510. FIG. 21B shows a cross-sectional view of the head 510 comprising first end 511, second end 512, splines 513, external tapered portion 514, abutments 515 having first ramped portion 515' and second ramped portion 515", inner wall 516, base 517, internal generally tapered portion 518 and internal essentially non-tapered portion 519. FIG. 21C shows a top view of head 510, and visible are splines 513, abutments 515 having first ramped portion 515' and second ramped portion 515", inner wall 516, base 517, internal generally tapered portion 518 and internal passageway 520.

FIG. 22A, FIG. 22B and FIG. 22C show different views of the body 530 of torque limited fitting 500 shown in FIG. 19 and FIG. 20. FIG. 22A shows a side view of body 530 comprising first end 531, second end 532, head portion 533, first external essentially non-tapered portion 534, first external generally tapered portion 535, second external essentially non-tapered portion 536, external lip 537, third external essentially non-tapered portion 538, second external generally tapered portion 539, fourth external essentially non-tapered portion 540 and external threaded portion 541. FIG. 22B shows a cross-sectional view of body 530 comprising first end 531, second end 532, head portion 533, first external essentially non-tapered portion 534, first external generally tapered portion 535, second external essentially non-tapered portion 536, external lip 537, third external essentially non-tapered portion 538, second external generally tapered portion 539, third external essentially non-tapered portion 540, external threaded portion 541, abutment 542, slot 543, internal generally tapered portion 544 and internal passageway 545 through the body 530. FIG. 22C shows a top view of body 530 comprising abutments 542 having first ramped portion 542' and second ramped portion 542", slots 543, internal generally tapered portion 544 and internal passageway 545.

Figure 23:
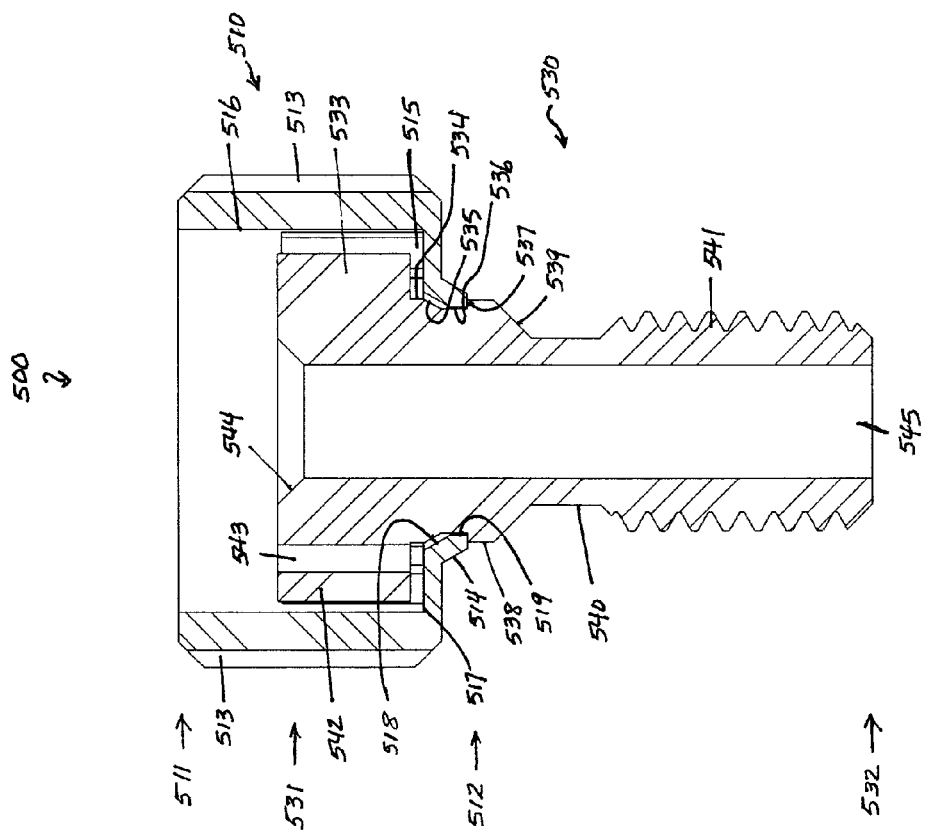
FIG. 23. A cross-sectional view of the torque limited fitting of FIG. 19 upon assembly.

Referring now to FIG. 23, a cross-sectional view of torque limited fitting 500 shown in FIG. 19 and FIG. 20 is depicted upon assembly of head 510 and body 530. Once again head 510 comprises first end 511, a second end 512, external splines 513, an external generally tapered portion 514 proximal the second end 512 of the head 510, abutment 515, inner wall 516, base 517 internal generally tapered portion 518 and internal essentially non-tapered portion 519, and body 530 comprises first end 531, second end 532, head portion 533, first external essentially non-tapered portion 534, first external generally tapered portion 535, second external essentially non-tapered portion 536, external lip 537, third external essentially non-tapered portion 538, second external generally tapered portion 539, third external essentially non-tapered portion 540, external threaded portion 541, abutment 542, slot 543, internal generally tapered portion 544 and internal passageway 545 through the body 530. As seen in FIG. 23, upon assembly external generally tapered portion 514 of head 510 engages lip 537 of body 530, which prevents separation of head 510 and body 530 of torque limited fitting 500 during normal operating conditions.

Figure 24:
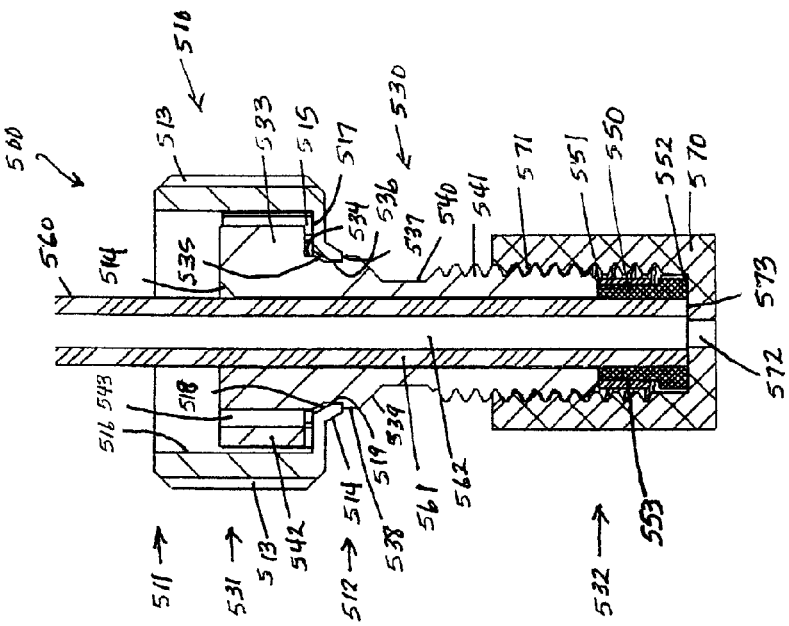
FIG. 24. A cross-sectional view of the fitting assembly of FIG. 23 when assembled with a ferrule, a lock ring and tubing in a port.

FIG. 24 shows a cross-sectional view of the torque limited fitting 500 with head 510 and body 530 shown in FIG. 23 with a piece of tubing 560 placed in the passageway 545 (not visible in FIG. 24) of the body 530 and engaged with ferrule 550 and lock ring 553 in a port 570. As described previously head 510 comprises first end 511, second end 512, external splines 513, external generally tapered portion 514 proximal the second end 512 of the head 510, abutment 515, inner wall 516, base 517 internal generally tapered portion 518 and internal essentially non-tapered portion 519, and body 530 comprises first end 531, second end 532, head portion 533, first external essentially non-tapered portion 534, first external generally tapered portion 535, second external essentially non-tapered portion 536, external lip 537, third external essentially non-tapered portion 538, second external generally tapered portion 539, third external essentially non-tapered portion 540, external threaded portion 541, abutment 542, slot 543, and internal generally tapered portion 544. Ferrule 550 comprises first end 551, second end 552, and passageway (not visible in FIG. 24) through the ferrule 550. Tubing 560 comprises wall 561 and passageway 562. Upon assembly external generally tapered portion 514 of head 510 acts to keep head 510 and body 530 engaged through interaction with lip 537 of body 530. Port 570 comprises internal threaded portion 571, passageway 572 and face 573. Torque limited fitting 500 is engaged in port 570 through interaction of the external threaded portion 541 of body 530 of torque limited fitting 500 and the internal threaded portion 571 of the port 570, with second end 552 of ferrule 550 and tubing 560 held flush against face 573 of the port 570.

Functionally, when the head 510 is rotated, the abutments 542 on the outer walls of the slots 543 in the head portion 533 of the body 530 interfere with the abutments 515 on the inner wall 516 of the head 510. This interference allows torque to be transferred to the external threaded portion 541 of the body 530, which engages the internal threaded portion 571 in the fluidic port 570. This in turn creates an axial force on the ferrule 550 at the external threaded portion 541 proximal the second end 532 of the body 530. When a predetermined torque value is reached, each abutment 542 on the head portion 533 of the body 530 is forced radially into the center of the body 530 (i.e., the slot 542 collapses; this action acts like a spring, similar to a leaf spring in a car). The outer wall of the slot 543 is basically a beam fixed on each end, as opposed to a lever, which is a cantilevered beam, fixed on one end. This deflection allows the abutments 515 on the inner wall 516 of the head 510 to snap over, and therefore not allow a higher torque to be transferred to the external threaded portion 541 of the body 530 and the ferrule 550.

While the present invention has been shown and described in various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:
1. A torque limited fitting for use in an analytical instrument system, comprising:
   (a) a head having a first end and a second end and a passageway therethrough, an inner wall having at least a first internal abutment; and
   (b) a body having a first end, a second end, a head portion comprising at least a first external abutment, an external lip proximal to the head portion of said body, at least one slot therein, and a passageway therethrough, wherein said external lip of said body is adapted to securely engage with a portion of said head proximal to the second end of said head.

2. The torque limited fitting according to claim 1, wherein said at least a first internal abutment comprises a first ramped portion and a second ramped portion.

3. The torque limited fitting according to claim 2, wherein said first ramped portion is steeper than said second ramped portion.

4. The torque limited fitting according to claim 1, wherein said head comprises a plurality of internal abutments.

5. The torque limited fitting according to claim 4, wherein said head comprises two internal abutments.

6. The torque limited fitting according to claim 1, wherein said at least a first external abutment comprises a first ramped portion and a second ramped portion.

7. The torque limited fitting according to claim 6, wherein said first ramped portion is steeper than said second ramped portion.

8. The torque limited fitting according to claim 1, wherein said body comprises a plurality of external abutments.

9. The torque limited fitting according to claim 1, wherein said body further comprises a first external non-tapered portion, a first external tapered portion and a second external non-tapered portion between said head of said body and said external lip.

10. The torque limited fitting according to claim 9, wherein said body further comprises a third external non tapered portion, a second external tapered portion and a fourth external non-tapered portion between said external lip and said external threaded portion.

11. The torque limited fitting according to claim 1, wherein the angle of said external tapered portion of said head is about 60° included angle.

12. The torque limited fitting according to claim 9, wherein the angle of said first external tapered portion of said body is about 60° included angle.

13. The torque limited fitting according to claim 10, wherein the angle of said second external tapered portion of said body is about 90° included angle.

14. The torque limited fitting according to claim 1, wherein said head or said body comprises polyetheretherketone.

15. The torque limited fitting according to claim 1, further comprising at least one tube extending through the internal passageway of said body.

16. An analytical instrument system comprising at least one torque limited fitting comprising:
 a) a head having a first end and a second end and a passageway therethrough, a portion having an outer diameter and an inner diameter and proximal to said second end of the head, an inner wall having at least a first internal abutment; and
 b) a body having a first end, a second end, a head portion comprising at least a first external abutment, an external lip proximal to said head of said body, and a passageway therethrough, wherein said external lip of said body has an outer diameter greater than the inner diameter of the portion of said head and smaller than the outer diameter of the portion of said head, and is adapted to securely engage with the head portion.

17. The torque limited fitting according to claim 1, wherein said body comprises at least one biocompatible material.

18. The analytical instrument system according to claim 16, wherein said analytical instrument system comprises a liquid chromatography, gas chromatography, ion chromatography, in vitro diagnostic analysis or environmental analysis system.

19. The analytical instrument system according to claim 16, further comprising a ferrule comprising an internal passageway located proximal the second end of said body of said torque limited fitting.

20. The analytical instrument system according to claim 19, further comprising at least one tube extending through the internal passageway of said body and the internal passageway of said ferrule.

21. The analytical instrument system according to claim 16, wherein said analytical instrument system comprises at least one of a liquid chromatography, gas chromatography, ion chromatography, invitro diagnosis analysis, or environmental analysis system.

22. A method of connecting tubing in an analytical instrument system comprising connecting a torque limited fitting and a ferrule comprising a tube extending therethrough to a port, fitting or component of said analytical instrument system; wherein said torque limited fitting comprises:
 a) a head having a first end and a second end and a passageway therethrough, a portion proximal to said second end of the head, and an inner wall comprising at least a first internal abutment; and
 b) a body having a first end, a second end, a head portion comprising at least a first external abutment, an external lip proximal to the head portion of said body, at least one slot therein, a threaded portion, and a passageway therethrough, wherein said external lip of said body is adapted to securely engage with said portion of said head;
 wherein said port, fitting or component comprises a threaded portion, and wherein said threaded portion of said port, fitting or component is adapted to securely engage with said threaded portion of said body.

23. The method according to claim 22, wherein said analytical instrument system comprises a liquid chromatography, gas chromatography, ion chromatography, in vitro diagnostic analysis or environmental analysis system.

24. A fitting assembly for use in an analytical instrument system, comprising:
 a. a head having a first end and a second end and a passageway therethrough, a portion proximal to said second end of the head, an inner wall comprising a plurality of internal abutments; and
 b. a body having a first end, a second end, a head portion comprising a plurality of external abutments, said body defining a plurality of slots therein, said external abutments of said body proximal to said slots, an external lip proximal to said head portion of said body, and a passageway therethrough, wherein said external lip of said body is adapted to securely engage with said portion of said head.

25. The fitting assembly according to claim 24 wherein the internal abutments of said head and the external abutments of said body are adapted to prevent transfer of more than a predetermined torque when said head and said body are rotated relative to one another.

26. The fitting assembly according to claim 25 wherein the internal abutments of said head and the external abutments of said body comprise selected shapes to provide a predetermined maximum torque value when said head and said body are rotated relative to one another.

27. The fitting assembly according to claim 24 wherein said head and said body are adapted so that when a predetermined torque is applied, at least one of the abutments of said body deflects radially inward.

28. The method according to claim 22 wherein said head and said body are adapted so that when a predetermined torque is applied, at least one of the abutments of said body deflects radially inward.

29. The torque limited fitting according to claim 1 wherein the internal abutment of said head and the external abutment of said body are adapted to prevent transfer of more than a predetermined torque when said head and said body are rotated relative to one another.

30. The torque limited fitting according to claim 1 wherein said head and said body are adapted so that when a predetermined torque is applied, at least one abutment of said body deflects radially inward.

31. The torque limited fitting according to claim 1 wherein said head and said body are adapted to prevent transfer of more than a predetermined maximum torque.

32. The analytical instrument system according to claim 16 wherein the internal abutment of said head and the external abutment of said body are adapted to prevent transfer of more than a predetermined torque to the torque limited fitting.

33. The analytical instrument system according to claim 16 wherein said head and said body are adapted so that when a predetermined torque is applied, at least one abutment of said head deflects radially inward.

34. The analytical instrument system according to claim 16 wherein said head and said body are adapted to prevent transfer of more than a predetermined maximum torque.

35. The method according to claim 22 wherein the internal abutment of said head and the external abutment of said body are adapted to prevent transfer of more than a predetermined maximum torque to a fitting assembly when rotating said head and said body relative to one another.

36. The method according to claim 22 wherein said head and said body are adapted to prevent transfer of more than a predetermined maximum torque value.

37. A fitting assembly for use in an analytical instrument system, comprising:
- a head having a first end and a second end and a passageway therethrough, a first portion proximal to the second end of the head, and an inner wall comprising at least a plurality of internal abutments; and
- a body having a first end, a second end, a head portion comprising a plurality external abutments and defining at least a plurality of slots therein, with the external abutments of said body proximal to said slots, an external lip proximal to the head portion of said body, a threaded portion, and a passageway therethrough, wherein said external lip of said body is adapted to securely engage with said first portion of said head, and wherein the internal abutments of said head and the external abutments of said body are adapted to prevent a user from applying more than a predetermined torque when rotating said head and said body relative to one another.

38. The fitting assembly according to claim 37 wherein said head and said body are adapted so that when the predetermined torque is reached when said body and said head are rotated relative to one another, at least one of the abutments of at least one of said head and said body deflects radially inward.

39. The fitting assembly according to claim 37 wherein said body and said head are adapted so that a leak-free and zero-volume connection can be obtained without applying a torque exceeding the predetermined torque.

40. The fitting assembly according to claim 39 wherein said body comprises a biocompatible material.

41. The fitting assembly according to claim 40 wherein said body and said head each comprise polyetheretherketone.

42. The torque limited fitting according to claim 37 wherein the plurality of slots comprises a slot which extends radially through a portion of the body.

43. The torque limited fitting according to claim 37 wherein the plurality of slots comprises a slot which comprises a hollow portion of a wall portion of the body.

44. A fitting assembly for use in an analytical instrument system, comprising:
- a head having a first end and a second end and a passageway therethrough, and an inner wall comprising at least a plurality of internal abutments, wherein at least one of the internal abutments has a ramped portion; and
- a body having a first end, a second end, a head portion comprising a plurality of external abutments, and having at least one slot extending through a portion of said body, and having a passageway therethrough, wherein at least a portion of the first end of said body is adapted to removably fit within a portion of the second end of said head, and wherein the internal abutments of said head and the external abutments of said body are adapted to cooperate so that at least one of the external abutments flexes inwardly when more than a predetermined torque is applied, thereby preventing transfer of more than the predetermined torque.

45. The fitting assembly according to claim 44 wherein the slot extends radially through a portion of said body.

46. The fitting assembly according to claim 44 wherein the slot comprises a hollow portion of a wall of the body.

* * * * *